(12) United States Patent
Sugawara et al.

(10) Patent No.: US 6,184,245 B1
(45) Date of Patent: Feb. 6, 2001

(54) CYCLIC KETONE DERIVATIVES AND THEIR MEDICAL APPLICATIONS

(75) Inventors: Yuji Sugawara; Hideki Kawai; Tsuyoshi Matsumoto, all of Kamakura; Kiyoshi Okano, Koza-gun; Satoko Takizawa, Fujisawa, all of (JP)

(73) Assignee: Toray Industries Inc., Tokyo (JP)

( * ) Notice: Under 35 U.S.C. 154(b), the term of this patent shall be extended for 0 days.

(21) Appl. No.: 09/317,925

(22) Filed: May 25, 1999

Related U.S. Application Data

(63) Continuation of application No. PCT/JP98/04317, filed on Sep. 25, 1998.

(30) Foreign Application Priority Data

Sep. 26, 1997 (JP) .................................... 9-262033

(51) Int. Cl.$^7$ ...................... A61K 31/38; A61K 31/335; C07D 309/10; C07D 333/04; C07D 333/10
(52) U.S. Cl. .................. 514/444; 514/438; 514/432; 514/449; 514/675; 549/292; 549/28; 549/60; 549/418
(58) Field of Search .................... 514/183, 432, 514/438, 444, 449, 461, 675; 549/28, 62, 66, 78, 83, 292, 418, 425, 483, 496, 504, 505, 59, 60

(56) References Cited

U.S. PATENT DOCUMENTS 3,489,774 * 1/1970 Kuhn et al. ...................... 549/418

FOREIGN PATENT DOCUMENTS

| 0 841 063 A1 | 5/1998 | (EP) . |
| 5046666 | * 4/1975 | (JP) . |
| 9735565 | * 10/1997 | (WO) . |

OTHER PUBLICATIONS

STN search report, Registry no's in WO 9735565 and JP 50046666 and US3489774, Aug. 30, 1999.*
Rowley et al J. Med. Chem. 1993, 36, 3386–3396 3–Acyl–4–hydroxyquinolin–2 (1H)–ones. Systemically etc.

* cited by examiner

Primary Examiner—Alan L. Rotman
Assistant Examiner—Rita Desai
(74) Attorney, Agent, or Firm—Nixon & Vanderhye

(57) ABSTRACT

The present invention relates to cyclic ketones represented by the following formula

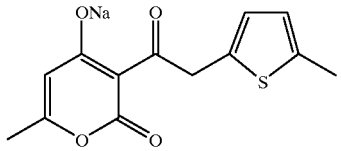

and to drugs in which an effective component is such a cyclic ketone or a pharmacologically acceptable salt thereof.

Figure 1:
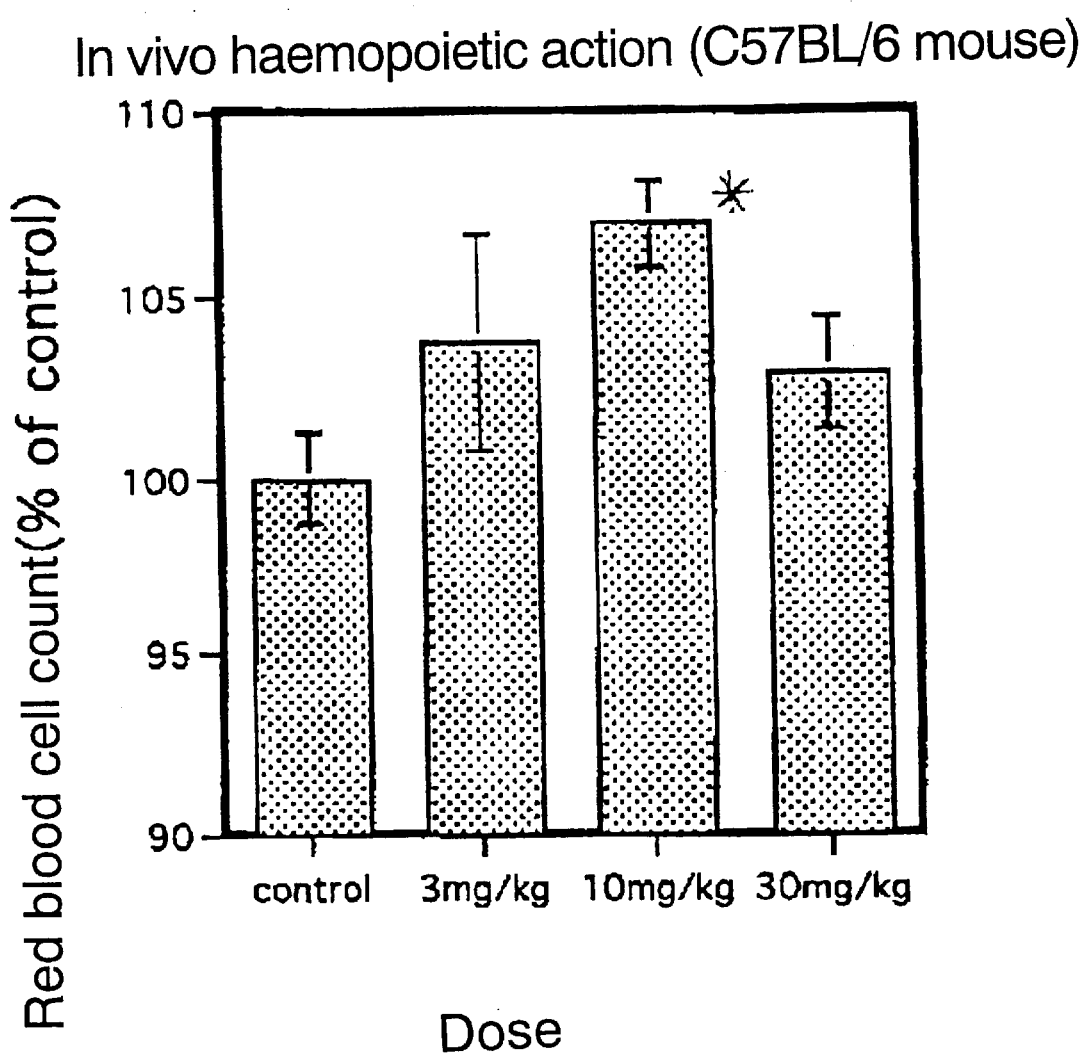

The cyclic ketones of the present invention encourage the production of blood platelets, leukocytes and erythrocytes, and can be employed in the prevention or treatment of cytopaenia brought about by cancer chemotherapy, radiotherapy or drug therapy, or by immunological abnormality, anaemia and the like.

9 Claims, 1 Drawing Sheet

CYCLIC KETONE DERIVATIVES AND THEIR MEDICAL APPLICATIONS

This application is a continuation of PCT/JP98/04317 filed Sep. 25, 1998 and also claims priority of Japanese patent application 262033/97 filed Sep. 26, 1997.

TECHNICAL FIELD

The present invention relates to drugs and in particular to haemopoietic agents in which a cyclic ketone derivative or pharmacologically acceptable salt thereof is an effective component.

TECHNICAL BACKGROUND

Cyclic ketone derivatives include lactones and lactams.

The lactones are known in the form of natural materials such as carolic acid and carolinic acid, and as synthetic materials such as the compounds described in *J. Chem. Soc. Perkin Trans. I*, 14, 1485–1491 (1976) and *Synth. Comm.*, 22(6), 809–816 (1992). As lactams, there are known, for example, the compounds disclosed in Japanese Unexamined Patent Publication (Kokai) Nos 2-279691, 4-49289, 2-48591 and 1-313488, *Chem. Pharm. Bull.*, 32(10), 4197–4204 (1984), *Pharmazie*, 43(7), 473–474 (1988), *Monatsh. Chem.*, 123(1–2), 93–98 (1992), *J. Inorg. Biochem.*, 24(3), 167–181 (1985), *J. Am. Chem. Soc.*, 107(18), 5219–5224 (1985), *J. Org. Chem.*, 50(8), 1344–1346 (1985) and *Chem. Rev.*, 95, 1981–2001 (1995).

With regard to the applications of the lactones, the compounds described for example in Japanese Unexamined Patent Publication (Kokai) No. 5-43568 and EP 0508690 are known as anti-inflammatory agents with phospholipase $A_2$ inhibitory activity; the compounds described in *Archive des Pharmazie* (Weinhelm, Ger.) (1983), 316(2), 115–120 are known as anticoagulants; and the compounds described in *J. Anitbiot.*, (1994), 47(2), 143–7 are known as an anti-AIDS drug with HIV-protease inhibitory activity. With regard to the applications of the lactams, the compounds described in for example *Chem. Pharm. Bull.*, 32(10), 4197–4204 (1984) are known as drugs with antimicrobial activity and the compounds described in *Antibiot.*, 33(2), 173–181 (1980) are known as anaerobic antibiotics.

However, cyclic ketone derivatives with a haemopoietic action are totally unknown. The present invention has the objective of offering cyclic ketone derivatives with an outstanding haemopoietic action.

DISCLOSURE OF THE INVENTION

The aforesaid objective is realized by the present invention as described below.

Specifically, the present invention relates to ketone derivatives represented by the following general formula (I)

(where $R_1$ to $R_8$ represent a hydrogen atom or a substituent group,

X represents O, S, $CH_2$ or NH, and

Y represents O or S) and pharmacologically acceptable salts thereof, and to drugs, in particular haemopoietic agents, containing a ketone represented by general formula (I) or pharmacologically acceptable salt thereof.

In particular, in general formula (I), $R_1$, $R_2$ and $R_3$ are independently a hydrogen atom, fluorine atom, chlorine atom, bromine atom, $C_1$ to $C_{10}$ alkyl group, $C_1$ to $C_{10}$ alkenyl group, $C_1$ to $C_{10}$ alkynyl group, $C_6$ to $C_{12}$ aryl group, $C_6$ to $C_{12}$ arylalkyl group, $C_6$ to $C_{12}$ alkylaryl group, $C_6$ to $C_{12}$ arylalkenyl group, or $-(CH_2)_p Z$ (where p represents an integer in the range 0 to 3, and Z represents a cyano group, carboxyl group, methylthio group, phenylthio group, trifluoromethyl group, methylthiomethyl group or nitro group), or $R_1$ and $R_2$ may together form $-CH=CH-CH=CH-$ or $-(CH_2)_n-$ (where n represents an integer in the range 2 to 5), or $R_2$ and $R_3$ may together form $-(CH_2)_m-$ (where m represents an integer in the range 2 to 5) (but excluding the case where $R_1$, $R_2$ and $R_3$ are all substituents selected from the hydrogen atom, fluorine atom, chlorine atom and bromine atom), $R_4$ and $R_5$ respectively independently represent a hydrogen atom, fluorine atom, chlorine atom, bromine atom, $C_1$ to $C_6$ alkyl group, hydroxy group, $C_1$ to $C_6$ alkoxy group, carboxy group or $C_2$ to $C_{10}$ alkoxycarbonyl group, $R_6$ represents a hydrogen atom, fluorine atom, chlorine atom, bromine atom, $C_1$ to $C_{10}$ alkyl group, $C_6$ to $C_{12}$ aryl group, $C_6$ to $C_{12}$ arylalkyl group, $C_6$ to $C_{12}$ alkylaryl group, $C_6$ to $C_{12}$ arylalkenyl group, or $-(CH_2)_q G$ (where q represents an integer in the range 1 to 3, and G represents a hydroxy group or $C_2$ to $C_{10}$ alkoxycarbonyl group), $R_7$ represents a hydrogen atom, fluorine atom, chlorine atom, bromine atom, $C_1$ to $C_{10}$ alkyl group, $C_6$ to $C_{12}$ aryl group, carboxy group or $C_2$ to $C_{10}$ alkoxycarbonyl group, or $R_6$ and $R_7$ together represent $-CH=CH-CH=CH-$ or $-(CH_2)_l-$ (where l represents an integer in the range 2 to 5), and $R_8$ represents a hydrogen atom or $C_1$ to $C_{10}$ alkyl group and, more preferably, $R_1$ to $R_5$ are independently a hydrogen atom, fluorine atom, chlorine atom, bromine atom, $C_1$ to $C_{10}$ alkyl group, or substituted or unsubstituted phenyl group, $R_6$ and $R_7$ are independently a hydrogen atom, fluorine atom, chlorine atom, bromine atom, $C_1$ to $C_{10}$ alkyl group, or substituted or unsubstituted phenyl group or $R_6$ and $R_7$ together form $-CH=CH-CH=CH-$ or $-(CH_2)_l-$ (where l represents an integer in the range 2 to 5), and $R_8$ is a hydrogen atom or $C_1$ to $C_{10}$ alkyl group.

Optimum Mode for Practising the Invention

The $C_1$ to $C_{10}$ alkyl groups in general formula (I) may be straight-chain, branched or cyclic, and examples are methyl, ethyl, n-propyl, isopropyl, n-butyl, isobutyl, sec-butyl, tert-butyl, n-pentyl, isopentyl, neopentyl, tert-pentyl, n-hexyl, n-heptyl, n-octyl, n-nonyl, cyclopropyl, cyclobutyl, cyclopentyl, cyclohexyl, cycloheptyl, cyclooctyl, cyclononyl and the like. The $C_1$ to $C_{10}$ alkenyl groups may be straight-chain or branched, and include isomers pertaining to the double bond (E or Z isomers). Examples are ethenyl, 2-propenyl, 2-butenyl, 2-pentenyl, 2-hexenyl, 2-heptenyl, 2-octenyl, 1,3-butadienyl, 1,3-pentadienyl, 1,3-hexadienyl, 1,4-pentadienyl, 1,4-hexadienyl, 1,4-heptadienyl, 1,3,5-hexatrienyl and the like. The $C_1$ to $C_{10}$ alkynyl groups may be straight-chain or branched, and examples are propynyl, butynyl, pentynyl, hexylnyl, heptynyl, octynyl and the like.

The aryl group in the $C_6$ to $C_{12}$ aryl groups, $C_6$ to $C_{12}$ arylalkyl groups, $C_6$ to $C_{12}$ alkylaryl groups and $C_6$ to $C_{12}$ arylalkenyl groups may be substituted with one, or more than one, halogen atom such as a chlorine atom, bromine atom or fluorine atom, hydroxy group, nitro group, methoxy, ethoxy or other such alkoxy group, carboxyl group, carbomethoxy, carboethoxy group or other such carboalkoxy group, cyano group, trifluoromethyl group, methylthio or other such alkylthio group, or phenylthio group.

Examples of the $C_6$ to $C_{12}$ aryl groups are phenyl, naphthyl, biphenyl and the like, and also aryl groups mono-substituted with a chlorine atom, bromine atom, fluorine atom, hydroxy group, nitro group, methoxy group, ethoxy group, carboxyl group, carbomethoxy group, carboethoxy group, cyano group, trifluoromethyl group, methylthio group, phenylthio group or the like, such as 2-chlorophenyl, 3-chlorophenyl, 4-chlorophenyl, 2-bromophenyl, 3-bromophenyl, 4-bromophenyl, 2-hydroxyphenyl, 3-hydroxyphenyl, 4-hydroxyphenyl, 2-nitrophenyl, 3-nitrophenyl, 4-nitrophenyl, 2-methoxyphenyl, 3-methoxyphenyl, 4-methoxyphenyl, 2-cyanophenyl, 3-cyanophenyl, 4-cyanophenyl, 2-carbomethoxyphenyl, 3-carbomethoxyphenyl, 4-carbomethoxyphenyl and the like; or disubstituted with the aforesaid groups, such as 2,3-dichlorophenyl, 2,4-dichlorophenyl, 3,4-dichlorophenyl, 2,3-dihydroxyphenyl, 2,4-dihydroxyphenyl, 3,4-dihydroxyphenyl, 2,3-dimethoxyphenyl, 2,4-dimethoxyphenyl, 3,4-dimethoxyphenyl, 2-chloro-3-bromophenyl, 2-chloro-3-hydroxyphenyl, 2-chloro-3-cyanophenyl, 2-chloro-3-methoxyphenyl, 2-hydroxy-3-chlorophenyl, 2-methoxy-3-chlorophenyl and the like; or trisubstituted with the aforesaid groups, such as 2,3,4-trichlorophenyl, 2,3,4-tribromophenyl, 2,3,4-trifluorophenyl, 2-chloro-3-hydroxy-4-methoxyphenyl, 2-hydroxy-3-hydroxy-4-methoxyphenyl and the like.

Examples of the $C_6$ to $C_{12}$ alkylaryl groups are 2-methylphenyl, 3-methylphenyl, 4-methylphenyl, 2-ethylphenyl, 3-ethylphenyl, 4-ethylphenyl and the like, or these mono-substituted with a chlorine atom, bromine atom, fluorine atom, hydroxy group, nitro group, methoxy group, ethoxy group, carboxyl group, carboethoxy group, carbomethoxy group, cyano group, trifluoromethyl group, methylthio group, phenythio group or the like, such as 2-methyl-3-chloro-phenyl, 2-methyl-4-chloro-phenyl, 2-methyl-5-chloro-phenyl, 3-methyl-2-chloro-phenyl, 3-methyl-4-chloro-phenyl, 3-methyl-5-chloro-phenyl, 4-methyl-2-chloro-phenyl, 4-methyl-2-chloro-phenyl, 4-methyl-3-chloro-phenyl, 4-methyl-5-chloro-phenyl, 2-methyl-3-bromo-phenyl, 2-methyl-4-bromo-phenyl, 2-methyl-5-bromo-phenyl, 3-methyl-2-bromo-phenyl, 3-methyl-4-bromo-phenyl, 3-methyl-5-bromo-phenyl, 4-methyl-2-bromo-phenyl, 4-methyl-2-bromo-phenyl, 4-methyl-3-bromo-phenyl, 4-methyl-5-bromo-phenyl, 2-methyl-3-methoxy-phenyl, 2-methyl-4-methoxy-phenyl, 2-methyl-5-methoxy-phenyl, 3-methyl-2-methoxy-phenyl, 3-methyl-4-methoxy-phenyl, 3-methyl-5-methoxy-phenyl, 4-methyl-2-methoxy-phenyl, 4-methyl-2-methoxy-phenyl, 4-methyl-3-methoxy-phenyl, 4-methyl-5-methoxy-phenyl, 2-ethyl-3-chloro-phenyl, 2-ethyl-4-chloro-phenyl, 2-ethyl-5-chloro-phenyl, 3-ethyl-2-chloro-phenyl, 3-ethyl-4-chloro-phenyl, 3-ethyl-5-chloro-phenyl, 4-ethyl-2-chloro-phenyl, 4-ethyl-2-chloro-phenyl, 4-ethyl-3-chloro-phenyl, 4-ethyl-5-chloro-phenyl, 2-ethyl-3-bromo-phenyl, 2-ethyl-4-bromo-phenyl, 2-ethyl-5-bromo-phenyl, 3-ethyl-2-bromo-phenyl, 3-ethyl-4-bromo-phenyl, 3-ethyl-5-bromo-phenyl, 4-ethyl-2-bromo-phenyl, 4-ethyl-2-bromo-phenyl, 4-ethyl-3-bromo-phenyl, 4-ethyl-5-bromo-phenyl, 2-ethyl-3-methoxy-phenyl, 2-ethyl-4-methoxy-phenyl, 2-ethyl-5-methoxy-phenyl, 3-ethyl-2-methoxy-phenyl, 3-ethyl-4-methoxy-phenyl, 3-ethyl-5-methoxy-phenyl, 4-ethyl-2-methoxy-phenyl, 4-ethyl-2-methoxy-phenyl, 4-ethyl-3-methoxy-phenyl, 4-ethyl-5-methoxy-phenyl and the like; or disubstituted with the aforesaid groups, such as 2-methyl-3-chloro-4-chloro-phenyl, 2-methyl-3-bromo-4-chloro-phenyl, 2-methyl-3-methoxy-5-chloro-phenyl, 3-methyl-2-chloro-4-hydroxy-phenyl and other such alkylaryl groups with an aryl group.

Examples of the $C_6$ to $C_{12}$ arylalkyl groups are benzyl, 2-phenylethyl, 3-phenylpropyl, 2-phenylpropyl, 4-phenylbutyl and the like, or these groups substituted with a chlorine atom, bromine atom, fluorine atom, hydroxy group, nitro group, methoxy group, ethoxy group, carboxyl group, carbomethoxy group, carboethoxy group, cyano group, trifluoromethyl group, methylthio group, phenythio group or the like, such as 2-phenyl-3-chloro-ethyl, 2-phenyl-4-chloro-ethyl, 2-phenyl-5-chloro-ethyl, 2-phenyl-3-bromo-ethyl, 2-phenyl-4-bromo-ethyl, 2-phenyl-5-bromo-ethyl, 2-phenyl-3-methoxy-ethyl, 2-phenyl-4-methoxy-ethyl, 3-phenyl-2-chloro-ethyl, 3-phenyl-4-chloro-ethyl, 3-phenyl-5-chloro-ethyl, 3-phenyl-2-bromo-ethyl, 3-phenyl-4-bromo-ethyl, 3-phenyl-5-bromo-ethyl, 3-phenyl-4-methoxy-ethyl, 2-phenyl-4-methoxy-ethyl and other such arylalkyl groups with an aryl group.

The $C_6$ to $C_{12}$ arylalkenyl groups will include isomers pertaining to the double bond (E, Z isomers), and examples are 2-phenylethenyl, 1-phenylethenyl, 3-phenyl-2-propenyl, 3-phenyl-1-propenyl and the like, or these groups substituted with a chlorine atom, bromine atom, fluorine atom, hydroxy group, nitro group, methoxy group, ethoxy group, carboxyl group, carbomethoxy group, carboethoxy group, cyano group, trifluoromethyl group, methylthio group, phenythio group or the like, such as 2-phenyl-3-chloro-ethenyl, 2-phenyl-4-chloro-ethenyl, 2-phenyl-5-chloro-ethenyl, 2-phenyl-3-bromo-ethenyl, 2-phenyl-4-bromo-ethenyl, 2-phenyl-5-bromo-ethenyl, 2-phenyl-3-methoxy-ethenyl, 2-phenyl-4-methoxy-ethenyl, 3-phenyl-2-chloro-ethenyl, 3-phenyl-4-chloro-ethenyl, 3-phenyl-5-chloro-ethenyl, 3-phenyl-2-bromo-ethenyl, 3-phenyl-4-bromo-ethenyl, 3-phenyl-5-bromo-ethenyl, 3-phenyl-4-methoxy-ethenyl, 2-phenyl-4-methoxy-ethenyl and other such arylalkenyl groups with an aryl group.

As examples of the $C_1$ to $C_6$ alkoxy groups, there are methoxy, ethoxy, propoxy, butoxy, pentoxy, hexoxy and the like.

Examples of the $C_2$ to $C_{10}$ alkoxycarbonyl groups are methoxycarbonyl, ethoxycarbonyl, propoxycarbonyl, butoxycarbonyl, pentoxycarbonyl, hexoxycarbonyl and the like.

Furthermore, as examples of —$(CH_2)_qG$ (where q represents an integer in the range 1 to 3, and G represents a hydroxy group or $C_2$ to $C_{10}$ alkoxycarbonyl group), there are hydroxycarbonylmethyl, hydroxycarbonylethyl, hydroxycarbonylpropyl, methoxycarbonylmethyl, methoxycarbonylethyl, methoxycarbonylpropyl, ethoxycarbonylmethyl, ethoxycarbonylethyl, propoxycarbonylmethyl, butoxycarbonylmethyl, pentoxycarbonylmethyl, hexoxycarbonylmethyl and the like.

When $R_8$ in general formula (I) of the present invention is a hydrogen atom, the following keto-enol tautomers are included.

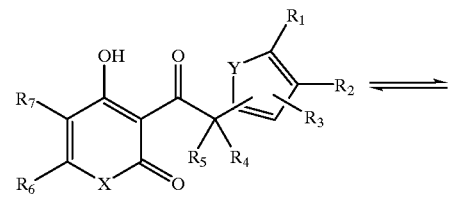

-continued

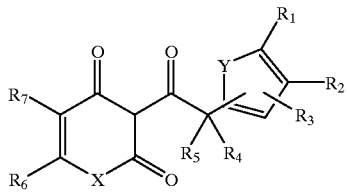

In the cyclic ketone derivatives (I) of the present invention, it is preferred that $R_1$ to $R_3$ be independently a hydrogen atom, fluorine atom, bromine atom, $C_1$ to $C_{10}$ alkyl group, or substituted or unsubstituted phenyl group (but not including those cases where $R_1$, $R_2$ and $R_3$ are all substituents selected from the hydrogen atom, fluorine atom, chlorine atom and bromine atom). $R_4$ is preferably a hydrogen atom and $R_5$ is preferably a hydrogen atom. $R_6$ is preferably a hydrogen atom, $C_1$ to $C_{10}$ alkyl group, or substituted or unsubstituted phenyl group, and $R_7$ is preferably a hydrogen atom, fluorine atom, chlorine atom, bromine atom, $C_1$ to $C_{10}$ alkyl group, or substituted or unsubstituted phenyl group. Again, the case where $R_6$ and $R_7$ are together —CH=CH—CH=CH— is also preferred. $R_8$ is preferably a hydrogen atom. X is preferably O or NH.

Specifically, preferred cyclic ketone derivatives are those where (1) $R_4$ and $R_5$ are hydrogen atoms, at least one of $R_1$ to $R_3$ is a $C_1$ to $C_{10}$ alkyl group, or substituted or unsubstituted phenyl group, while the remainder are a hydrogen atom, fluorine atom, chlorine atom or bromine atom, $R_6$ and $R_7$ are $C_1$ to $C_{10}$ alkyl groups, or substituted or unsubstituted phenyl groups, $R_8$ is a hydrogen atom, and X is O or NH, (2) $R_4$, $R_5$ and $R_7$ are hydrogen atoms, at least one of $R_1$ to $R_3$ is a $C_1$ to $C_{10}$ alkyl group, or substituted or unsubstituted phenyl group, while the remainder are a hydrogen atom, fluorine atom, chlorine atom or bromine atom, $R_6$ is a $C_1$ to $C_{10}$ alkyl group, or substituted or unsubstituted phenyl group, $R_8$ is a hydrogen atom, and X is O or NH, (3) $R_4$ and $R_5$ are hydrogen atoms, $R_7$ is a bromine atom or chlorine atom, at least one of $R_1$ to $R_3$ is a $C_1$ to $C_{10}$ alkyl group, or substituted or unsubstituted phenyl group, while the remainder are a hydrogen atom, fluorine atom, chlorine atom or bromine atom, $R_6$ is a $C_1$ to $C_{10}$ alkyl group, or substituted or unsubstituted phenyl group, $R_8$ is a hydrogen atom, and X is O or NH, (4) $R_4$ and $R_5$ are hydrogen atoms, $R_7$ is a carboxy group or $C_2$ to $C_{10}$ alkoxycarbonyl group, at least one of $R_1$ to $R_3$ is a $C_1$ to $C_{10}$ alkyl group, or substituted or unsubstituted phenyl group, while the remainder are a hydrogen atom, fluorine atom, chlorine atom or bromine atom, $R_6$ is a $C_1$ to $C_{10}$ alkyl group, or substituted or unsubstituted phenyl group, $R_8$ is a hydrogen atom, and X is O or NH, and (5) $R_4$ and $R_5$ are hydrogen atoms, $R_6$ and $R_7$ are together —CH=CH—CH=CH—, at least one of $R_1$ to $R_3$ is a $C_1$ to $C_{10}$ alkyl group, or substituted or unsubstituted phenyl group, while the remainder are a hydrogen atom, fluorine atom, chlorine atom or bromine atom, $R_8$ is a hydrogen atom, and X is O or NH.

More preferred examples are the cyclic ketone derivatives where (1) $R_1$, $R_2$, $R_4$, $R_5$, $R_7$ and $R_8$ are hydrogen atoms, $R_3$ and $R_6$ are a $C_1$ to $C_{10}$ alkyl group, and X is O or NH, (2) $R_1$, $R_2$, $R_4$, $R_5$ and $R_8$ are hydrogen atoms, $R_3$ and $R_6$ are a $C_1$ to $C_{10}$ alkyl group, $R_7$ is a bromine atom or chlorine atom, and X is O or NH, (3) $R_1$, $R_2$, $R_4$, $R_5$ and $R_8$ are hydrogen atoms, $R_3$ and $R_6$ are a $C_1$ to $C_{10}$ alkyl group, $R_7$ is a carboxy group or $C_2$ to $C_{10}$ alkoxycarbonyl group, and X is O or NH.

The cyclic ketone derivative (I) which is the effective component in the present invention can be used in medical applications in its free form or in the form of a pharmacologically acceptable salt.

As examples of the pharmacologically acceptable salts, there are base-addition salts and acid-addition salts. The base-addition salts are salts which retain the biological efficacy and characteristics of the free acid, without being biologically or otherwise undesirable, and include salts obtained from inorganic bases such as the sodium, potassium, lithium, ammonium, calcium and magnesium salts. They also include of course salts obtained from organic bases. For example, they include salts obtained from substituted amines such as primary amines, secondary amines, tertiary amines, natural substituted amines, cyclic amines and basic ion-exchange resins, specific examples of which are isopropylamine, trimethylamine, diethylamine, tripropylamine, ethanolamine, 2-dimethylaminoethanol, 2-diethylaminoethanol, trimethamine, dicyclohexylamine, lysine, arginine, histidine, caffeine, procaine, hydrabamine, choline, betaine, ethylenediamine, glucosamine, methylglucamine, theobromine, purine, piperazine, piperidine, N-ethylpiperidine, ornithine, polyamine resin and the like. Again, the acid-addition salts are salts which retain the biological efficacy and characteristics of the free base, without being biologically or otherwise undesirable, and they include inorganic acid salts such as the hydrochloride, sulphate, nitrate, hydrobromide, hydroborofluoride, phosphate, perchlorate and the like, and organic acid salts such as the oxalate, tartrate, lactate, acetate and the like. However, the pharmacologically acceptable salts of the present invention are not restricted to these.

Amongst the compounds of the present invention, in cases where there is an asymmetric carbon in the molecule, optical isomers will be present and, moreover, in cases where there are at least two asymmetric carbons diastereomers are present. The present invention will include these optical isomers and diastereomers. Furthermore, the invention will include stereoisomers.

The production of the cyclic ketone derivatives of the present invention can be carried out by known methods. For example, they can be produced by the methods disclosed in *J. Chem. Soc. Perkin Trans. I,* 121–129 (1987), *J. Org. Chem.,* 59, 488–490 (1994), *Bull. Chem. Soc. Japan,* 52, 3601–3605 (1979), *J. Chem. Soc. Perkin Trans. I,* 1225–1231 (1987), and *Chem. Pharm. Bull.,* 32(10), 4197–4204 (1984).

Specifically, they can be synthesized by the methods described below but the method of synthesis is not restricted thereto.

Amongst the compounds represented by general formula (I), the compounds (Ia) in which $R_8$ is a hydrogen atom are obtained by condensation between ketone derivatives represented by general formula (II) (here $R_6$ and $R_7$ have the same definitions as above) and the carboxylic acids or carboxylic acid derivatives represented by general formula (III) (here $R_1$, $R_2$, $R_3$, $R_4$ and $R_5$ have the same definitions as above, and $R_9$ is a $C_1$ to $C_{10}$ alkyl group or phenyl group).

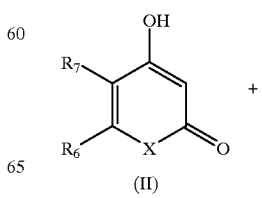

(II)

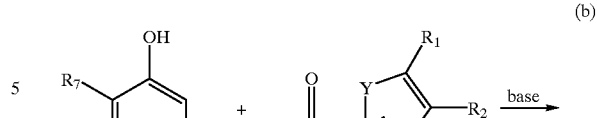
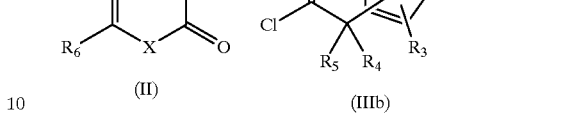
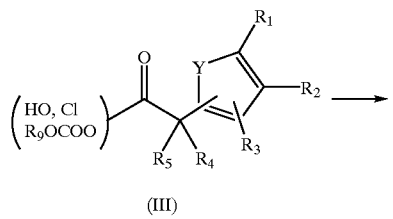

(III)

(Ia)

(Ia)

(Ia)

(Ib)

(In the above formulae, $R_1$ to $R_7$, X and Y have the same definitions as above.)

Where $R_9$ in general formula (III) is a $C_1$ to $C_{10}$ alkyl group, this may be a straight chain, branched or cyclic, and examples are methyl, ethyl, n-propyl, isopropyl, n-butyl, isobutyl, sec-butyl, tert-butyl, n-pentyl, isopentyl, neopentyl, tert-pentyl, n-hexyl, n-heptyl, n-octyl, n-nonyl, cyclopropyl, cyclobutyl, cyclopentyl, cyclohexyl, cycloheptyl, cyclooctyl, cyclononyl or the like.

The method of production in the present invention will now be explained in more specific terms.

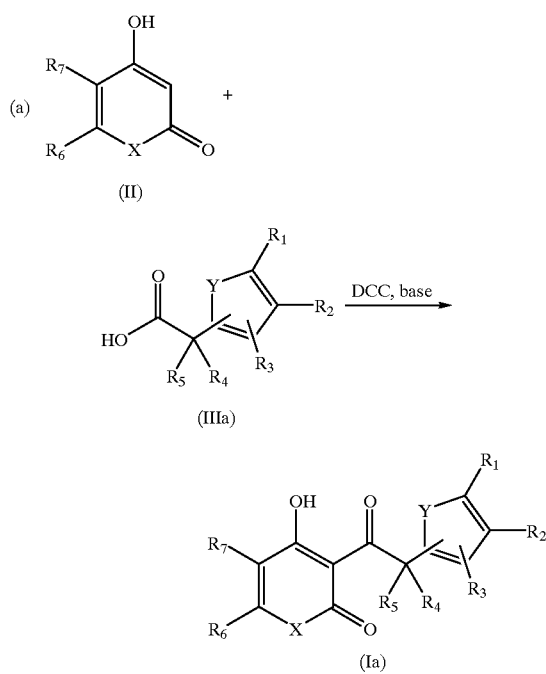

(a)

(II)

(IIIa)

(Ia)

(In the above formulae, $R_1$ to $R_8$, X and Y have the same definitions as above.)

The reaction between (II) and carboxylic acid (IIIa) can be carried out in the presence of a condensing reagent or base (Production Method (a)). From 1 to 10 equivalents, and preferably from 1 to 5 equivalents, of carboxylic acid (IIIa) is used and, as the solvent, there is preferably employed a hydrocarbon solvent such as toluene, benzene or the like, a halogen-based solvent such chloroform, dichloromethane, dichloroethane or the like, or a solvent mixture thereof. As the base, there is used an organic base such as triethylamine, diisopropylethylamine, proton sponge or other such tertiary amine, pyridine, dimethylaminopyridine, imidazole or the like, or an inorganic base such as potassium carbonate, sodium carbonate, sodium hydrogen carbonate, sodium hydroxide, potassium hydroxide or the like, preferably from 0.2 to 5 equivalents of an organic base such as triethylamine or other such tertiary amine, or dimethylaminopyridine. As the condensing reagent, there is used N,N'-dicyclohexylcarbodiimide (DCC), 1,1'-carbonyldiimidazole, bis(2-oxo-3-oxazolidinyl)phosphinic acid chloride or the like, preferably from 1 to 5 equivalents of DCC. Reaction can be conducted in the range −80° C. to 120° C., with favourable results being obtained from 0° C. to about 100° C. Furthermore, compound (Ia) can also be obtained using acid chloride (IIIb) (Production Method (b)). From 1 to 10 and preferably from 1 to 5 equivalents of acid chloride (IIIb) is used. As the reaction solvent, there is preferably employed a hydrocarbon solvent such as toluene, benzene or the like, a halogen-based solvent such chloroform, dichloromethane, dichloroethane or the like, or a solvent mixture thereof. As the base, there is used an organic base such as triethylamine, diisopropylethylamine, proton sponge or other such tertiary amine, pyridine, dimethylaminopyridine, imidazole or the like, or an inorganic base such as potassium carbonate, sodium carbonate, sodium hydrogen carbonate, sodium hydroxide, potassium hydroxide or the like, preferably from 0.2 to 5 equivalents of an organic base such as triethylamine or other such tertiary amine, or dimethylaminopyridine. The reaction can be conducted in the range −80° C. to 120° C., with favourable results being obtained from 0° C. to about 100° C.

Compound (Ib) where $R_8$ in general formula (1) is a $C_1$ to $C_{10}$ alkyl group can be produced by the reaction of compound (Ia) obtained by an aforesaid method with the corresponding alkyl halide in the presence of base. As the alkyl halide, there is used from 1 to 20 equivalents of an alkyl chloride, alkyl bromide or alkyl iodide, preferably from 1 to 10 equivalents of alkyl iodide.

As the reaction solvent, there can be used a hydrocarbon solvent such as benzene, toluene, xylene or the like, an ether solvent such as diethyl ether or tetrahydrofuran, or dimethylformamide. As the base, there can be used an inorganic base such as sodium hydroxide, potassium hydroxide, sodium hydride or the like, or an organic base such as triethylamine, pyridine or the like. The reaction can be conducted in the range −20° C. to 150° C., with favourable results being obtained from 0° C. to about 100° C.

The synthesis of carboxylic acids (IIIa) can be carried out by the methods described in *Synthesis*, 567–568 (1991), *J. Org. Chem.*, 41(17), 2835–2845 (1976), *Bull. Chem. Soc. Jpn.*, 52(7), 2013–2022 (1979), and *Tetrahedron Lett.*, 1383–1386 (1972), etc.

The compounds (II) are readily available as commercial products. The acid chlorides (IIIb) can be synthesized from the carboxylic acids (IIIa) using one of the usual chlorinating agents such as thionyl chloride or phosphorus oxychloride.

In cases where a therapeutic agent containing an effective amount of a cyclic ketone of the present invention is administered clinically, the administration can be carried out orally or parenterally. Administration forms include tablets, sugar-coated tablets, pills, capsules, powders, lozenges, solutions, suppositories and injections, and these can be produced by compounding with medically permitted fillers. The following can be given as examples of fillers. There are medically permitted fillers such as lactose, sucrose, glucose, sorbitol, mannitol, potato starch, amylopectin, various other types of starch, cellulose derivatives (for example carboxymethyl cellulose, hydroxyethyl cellulose and the like), gelatin, magnesium stearate, polyvinyl alcohol, polyethylene glycol wax, gum Arabic, talc, titanium dioxide, olive oil, peanut oil, sesame oil and other types of vegetable oil, liquid paraffin, neutral fatty base, ethanol, propylene glycol, physiological saline, sterilized water, glycerol, colouring agents, flavourings, thickeners, stabilizers, isotonic agents, buffers and the like.

In the present invention haemopoietic agent refers to a drug which, when administered to humans or animals, encourages the production of platelets, red blood cells, white blood cells and the like within the body, and which is used to prevent or treat cytopaenia brought about by cancer chemotherapy, radiotherapy, bone marrow transplantation and drug therapy, or by immunological abnormality or anaemia such as renal anaemia, haemorrhagic anaemia, haemolytic anaemia or deficiency anaemia. Moreover, the haemopoietic agents of the present invention can also be used in the field of treating aplastic anaemia, thrombocytopaenia, and hypoleukocytosis caused by infectious disease, viral disease or nutrition disorders, or idiopathic thrombocytopaenic purpura and the like. Furthermore, they can also be used for self-stored blood and the like.

It is also possible to use the haemopoietic agents of the present invention in combination with, for example, EPO which is a red blood cell boosting agent or G-CSF which is a leukocyte boosting agent, in the prevention or treatment of cytopaenia brought about by cancer chemotherapy, radiotherapy, bone marrow transplantation and drug therapy, or by immunological abnormality or anaemia such as renal anaemia, haemorrhagic anaemia, haemolytic anaemia or deficiency anaemia.

The amount of the therapeutic agent of the present invention employed will differ according to the symptoms, body weight, age and method of administration but, normally, there can be administered to an adult from 0.01 mg to 2000 mg per day.

EXAMPLES

Below, the present invention is explained in still more specific terms by providing examples.

Example 1

Synthesis of Compound 1: 3-{2-(5-methylthiophen-2-yl)}acetyl-4-hydroxy-6-methyl-2-pyrone

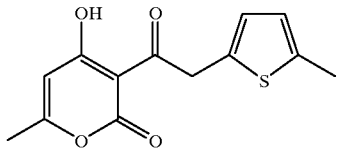

150 ml of acetic acid was added to 18.39 g (75 mmol) of manganese(II) acetate and, while maintaining at 80° C., 3.0 g (18.9 mmol) of potassium permanganate then added and stirring carried out for 30 minutes at 80° C. 27 g (225 mmol) of acetic anhydride was slowly added dropwise at this temperature, after which the mixture was cooled to room temperature. 7 ml (33 mmol) of triethyl methanetricarboxylate, 3.2 ml (33 mmol) of 2-methylthiophene and 4.92 g (60 mmol) of sodium acetate were added, and stirring carried out for 24 hours at 60° C. After cooling, 60 ml of water was added and extraction performed with toluene. Next, drying was carried out with anhydrous magnesium sulphate, followed by filtering and concentration. The residue was purified by column chromatography and 8.66 g (26.3 mmol, yield 79%) of the methanetricarboxylic acid adduct obtained. Colourless oil.

90 ml of 1 N aqueous sodium hydroxide solution was added to 8.66 g (26.3 mmol) of the methanetricarboxylic acid adduct obtained, and stirring carried out overnight at 80° C. When the reaction liquid was then cooled and acidified with concentrated hydrochloric acid, decarboxylation commenced. Stirring was carried out for 1 hour at 80° C., then extraction performed with ether, followed by drying with anhydrous sodium sulphate, filtering and concentration. 4.30 g (26.3 mmol, yield: 100%) of unpurified 5-methyl-2-thiopheneacetic acid was obtained. Brown crystals.

4.30 g (26.3 mmol) of the carboxylic acid, 3.46 g (27.4 mmol) of 4-hydroxy-6-methyl-pyrone, 6.24 g (30.2 mmol)

of N,N-dicyclohexylcarbodiimide (DCC) and 30 ml of toluene were stirred for 24 hours at room temperature. The insoluble material was filtered off and then concentration performed. The residue was purified by column chromatography and 4.32 g (16.3 mmol, yield: 59%) of the O-acyl compound obtained. 25 ml of chloroform was added to this, then 255 mg (2.05 mmol) of 4-dimethylaminopyridine (DMAP) added, and stirring carried out for 15 hours at 60° C. The reaction liquid was then concentrated, the reside dissolved in ethyl acetate and washed with dilute hydrochloric acid, after which drying was performed with anhydrous magnesium sulphate and then filtering and concentration performed. The residue was recrystallized from methanol and 1.35 g (5.10 mmol, yield: 31%) of target Compound 1 obtained. Pale brown crystals.

Compound 1
Melting point 117–118° C.
Elemental analysis
Compositional formula $C_{13}H_{12}O_4S$
Calculated C, 59.08; H, 4.58; S, 12.13
Measured C, 58.96; H, 4.63; S, 12.09
$^1$H-NMR (300 MHz, $CD_3OD$) δ=2.33 (d, 3H, J=0.55), 2.45 (s, 3H), 4.51 (s, 2H), 6.20 (d, 1H, J=0.55), 6.63 (m, 1H), 6.75 (d, 1H, J=3.29)
IR (KBr) $cm^{-1}$ 1709, 1651, 1560, 1460, 996
Mass (EI) 264 ($M^+$)

Example 2

Synthesis of Compound 2: 3-{2-(5-methylfuran-2-yl)}acetyl-4-hydroxy-6-methyl-pyrone

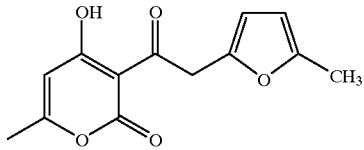

Synthesis of Compound 29:
3-{2-(3 -hexylthiophen-2-yl)}acetyl-4-hydroxy-6-methyl-pyrone and 3- {2-(4-hexylthiophen-2-yl)}acetyl-4-hydroxy-6-methylpyro 7.37 g (66.9 mmol) of 5-methylfurfural and 8.96 g (67.3 mmol) of rhodanine were suspended in 70 ml of acetic acid. To this suspension, there was added 17.69 g (215.6 mmol) of sodium acetate, and then stirring carried out for 1 hour at 90° C. After confirming that a red precipitate had been produced, the reaction suspension liquid was cooled to room temperature, and this was poured into 300 ml of water. After thorough stirring, the precipitate was filtered off, the residue washed with a further 50 ml of water and then the residue washed with 15 ml of 99.5% ethanol and 5 ml of diethyl ether. The residue was then dried and 11.4 g (50.6 mmol) of 5-methylfurfuralrhodanine obtained at a crude yield of 75%. Without further purification, this was used in the next reaction.
$^1$H-NMR (300 MHz, $CDCl_3$) δ=2.43 (3H, S), 6.228–6.242 (1H, m), 6.791–6.803 (1H, m), 7.34 (1H, s)

11.36 g (50.4 mmol) of the 5-methylfurfuralrhodanine was suspended in 120 ml of 10% aqueous sodium hydroxide solution, and refluxed for 2 hours. The reaction liquid was then cooled and crystals precipitated by pouring-in 4 N hydrochloric acid (200 ml) all in one go. The crystals were filtered off and dissolved in ether. This solution was washed in turn with 10% aqueous sodium thiosulphate solution and saturated salt solution, after which drying was performed with anhydrous sodium sulphate. By concentrating under reduced pressure, 8.00 g (43.4 mmol) of the target material was obtained at a crude yield of 86%.
$^1$H-NMR (300 MHz, $CDCl_3$) δ=2.396 (3H, m), 4.68 (1H, s), 6.19–6.21 (1H, m), 6.79–6.81 (1H, m), 7.658 (1H, s)

7.29 g (317 mmol) of small pieces of metal sodium were introduced over 2 hours into 180 ml of ethanol, and sodium ethoxide generated within the system. After stirring for a further 1 hour at room temperature, 20.4 g (284 mmol) of hydroxylamine hydrochloride was added at room temperature and stirring carried out for 50 minutes at room temperature. To this, there was added at room temperature 80 ml of an ethanol solution of 7.99 g (43.4 mmol) of the thioketocarboxylic acid obtained above. The mixture was refluxed for 3 hours and then, along with the precipitate, concentration was performed, after which the residue was dissolved in 80 ml of 5% aqueous sodium hydroxide solution and filtering carried out. After acidifying with 4 N hydrochloric acid, extraction was carried out five times with ether and, following drying with anhydrous magnesium sulphate, concentration was carried out under reduced pressure and 7.13 g of a mixture obtained. 100 ml of acetic anhydride and 100 ml of water were added to the 7.13 g of this oxime, and heating and refluxing carried out for 10 hours. Steam distillation was then directly carried out and the fraction obtained concentrated, and treated with dilute base. 0.70 g (5.8 mmol) of 5-methyl-2-furanacetonitrile was obtained at a yield of 13% for the two stages.

50 ml of 5% aqueous sodium hydroxide solution was added to the 0.70 g (5.8 mmol) of 5-methyl-2-furanacetonitrile thus obtained, and stirring carried out for 3 hours at 110° C. After cooling, the solution was acidified with acid and extracted with ether. This was washed with water and dried with magnesium sulphate, after which concentration was carried out and 0.62 g (4.4 mmol) of 5-methyl-2-furanacetic acid was obtained at a 76% yield.

0.62 g (4.4 mmol) of 5-methyl-2-furanacetic acid and 0.59 g (4.7 mmol) of 4-hydroxy-6-methyl-2-pyrone were dissolved in 20 ml of toluene, then 1.05 g (5.09 mmol) of DCC and 0.15 g (1.2 mmol) of DMAP added thereto, and stirring carried out for 2 hours at room temperature, following which stirring was carried out for 6 hours at 80° C. After cooling to room temperature, washing was carried out in turn with 1.0 N hydrochloric acid, water and saturated salt solution, followed by drying with anhydrous sodium sulphate. Concentration was then performed and 0.20 g of a mixture obtained. After carrying out chromatography with dichloromethane, and recrystallizing from methanol, 60 mg was obtained.

Compound 2
$^1$H-NMR (300 MHz, $CDCl_3$) δ=2.277–2.286 (m, 6H), 4.403 (s, 2H), 5.93 (m, 1H), 5.95 (d, J=0.8 Hz, 1H), 6.13–6.14 (d, J=2.7 Hz, 1H)

Example 3

Synthesis of Compound 3: 3-{2-(5-ethylfuran-2-yl)}acetyl-4-hydroxy-6-methyl-2-pyrone

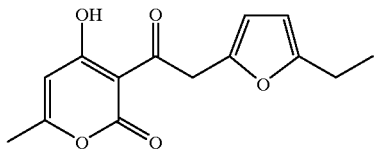

1.89 g (12.2 mmol) of 5-ethylfuranacetic acid, 1.55 g (12.3 mmol) of 4-hydroxy-6-methyl-2-pyrone, 2.80 g (13.5 mmol) of DCC and 149 mg (1.22 mmol) of DMAP were stirred together for 16 hours at 80° C. in 50 ml of toluene. The reaction liquid was cooled to room temperature, the insoluble material filtered off and then concentration performed. The residue was crudely purified by column chromatography (dichloromethane), after which recrystallization was carried out from diethyl ether. Compound 3 (0.84 g, 3.20 mmol, yield: 26%) was obtained. Pale yellow crystals.

Compound 3

Melting point 90–91° C.

Elemental analysis

Compositional formula $C_{14}H_{14}O_5$

Calculated C, 64.12; H, 5.38;

Measured C, 64.07; H, 5.42;

$^1$H-NMR (300 MHz, CDCl$_3$) δ=1.21 (t, 3H, J=7.69), 2.28 (d, 3H, J=0.73), 2.63 (q, 2H, J=7.69), 4.41 (s, 2H), 5.93–5.96 (m, 2H), 6.15 (d, 1H, J=2.93), 16.17 (s, 1H)

IR (KBr) cm$^{-1}$ 1715, 1651, 1560, 1462, 996, 774

Mass (EI) 262 (M$^+$)

Example 4

Synthesis of Compound 4: 3-{2-(3-methylthiophene-2-yl)}acetyl-4-hydroxy-6-methyl-2-pyrone

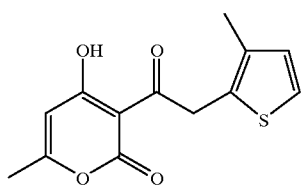

1.53 g (9.80 mmol) of 3-methylthiopheneacetic acid, 1.23 g (9.80 mmol) of 4-hydroxy-6-methyl-2-pyrone, 2.24 g (10.8 mmol) of DCC and 157 mg (1.28 mmol) of DMAP were stirred together for 16 hours at 60° C. in 40 ml of toluene. The reaction liquid was cooled to room temperature, the insoluble material filtered off and then concentration performed. The residue was crudely purified by column chromatography (dichloromethane), after which recrystallization was carried out from ethanol. Compound 4 (0.84 g, 3.19 mmol, yield : 33%) was obtained. Pale yellow crystals.

Compound 4

Melting point 93–94° C.

Elemental analysis

Compositional formula $C_{13}H_{12}O_4S$

Calculated C, 59.08; H, 4.58; S, 12.13

Measured C, 59.03; H, 4.62; S, 12.01

$^1$H-NMR (300 MHz, CDCl$_3$) δ=2.18 (s, 3H), 2.29 (d, 3H, J=0.73), 4.55 (s, 2H), 5.97 (t, 1H, J=0.73), 6.86 (d, 1H, J=5.13), 7.15 (d, 1H, J=5.13), 16.21 (s, 1H)

IR (KBr) cm$^{-1}$ 1719, 1653, 1551, 1454, 992

Mass (EI) 264 (M$^+$)

Example 5

Synthesis of Compound 5: 3-{2-(5-ethylfuran-2-yl)}acetyl-4-hydroxy-coumarin

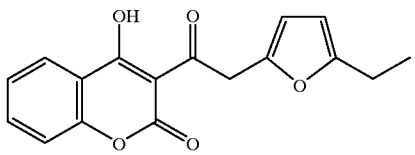

2.50 g (16.2 mmol) of 5-ethylfuranacetic acid, 2.62 g (16.2 mmol) of 4-hydroxy-coumarin, 3.70 g (17.9 mmol) of DCC and 204 mg (1.67 mmol) of DMAP were stirred together for 16 hours at 80° C. in 50 ml of toluene. The reaction liquid was then cooled to room temperature, the insoluble material filtered off and concentration performed. The residue was recrystallized from ethyl acetate, and Compound 5 (0.80 g, 2.68 mmol, yield: 16%) was obtained. Pale yellow crystals.

Compound 5

Melting point 80–82° C.

Elemental analysis

Compositional formula $C_{17}H_{14}O_5$

Calculated C, 68.45; H, 4.73

Measured C, 68.36; H, 4.76

$^1$H-NMR (300 MHz, CDCl$_3$) δ=1.22 (t, 3H, J=7.32), 2.64 (q, 2H, J=7.32), 4.54 (s, 2H), 5.96 (d, 1H, J=2.93), 6.29 (d, 1H, J=2.93), 7.31–7.38 (m, 2H), 7.72 (m, 1H), 8.07 (dd, 1H, J=1.10, 7.69), 17.18 (s, 1H)

IR (KBr) cm$^{-1}$ 1744, 1620, 1555, 1425, 986, 762

Mass (EI) 298 (M$^+$)

Example 6

Synthesis of Compound 6: 3-{2-(3-methylthiophene-2-yl)}acetyl-4-hydroxy-coumarin

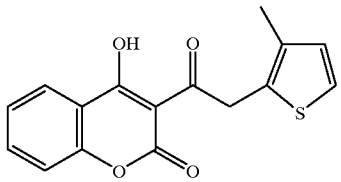

1.53 g (9.80 mmol) of 3-methylthiopheneacetic acid, 1.59 g (9.80 mmol) of 4-hydroxy-coumarin, 2.24 g (10.8 mmol) of DCC and 157 mg (1.29 mmol) of DMAP were stirred together for 16 hours at 60° C. in 40 ml of chloroform. The reaction liquid was cooled to room temperature, the insoluble material filtered off and then concentration performed. The residue was recrystallized from ethanol, and Compound 6 (1.04 g, 3.46 mmol, yield : 35%) was obtained. Pale yellow crystals.

Compound 6

Melting point 125–128° C.

Elemental analysis

Compositional formula $C_{16}H_{12}O_4S$

Calculated C, 63.99; H, 4.03; S, 10.68

Measured C, 63.96; H, 4.08; S, 10.66

$^1$H-NMR (300 MHz, CDCl$_3$) δ=2.21 (s, 3H), 4.68 (s, 2H), 6.88 (d, 1H, J=5.13), 7.17 (d, 1H, J=5.13), 7.32–7.39 (m, 2H), 7.72 (m, 1H), 8.07 (dd, 1H, J=1.83, 8.05), 17.22 (s, 1H)

IR (KBr) cm$^{-1}$ 1717, 1609, 1557, 1421

Mass (EI) 300 (M$^+$)

Example 7

Synthesis of Compound 7: 3-{2-(4,5-dimethylfuran-2-yl)}acetyl-4-hydroxy-6-methylpyrone

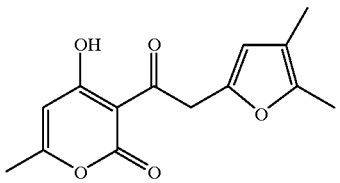

A liquid mixture of 10.4 g (84.0 mmol) of 4,5-dimethylfuran-2-aldehyde, 60 ml of acetic acid, 11.0 g (82.6 mmol) of rhodanine and 19.8 g (241 mmol) of sodium acetate was stirred for 1.5 hours at 100° C. Ice water was added to the reaction liquid, and filtering and washing with water performed. 200 ml of 10% aqueous sodium hydroxide solution was added to the solid obtained, and stirring carried out for 2 hours at 100° C. The reaction liquid was then cooled, and acidification performed with concentrated hydrochloric acid. The precipitate which was deposited was filtered off and washed with water. Drying was performed using a vacuum pump and 15.8 g (79.6 mmol) of 3-(4,5-dimethyl-2-furano)thiopyruvic acid (yellow powder) obtained.

15.8 g (about 79.6 mmol) of 4,5-dimethylfuran-2-thiopyruvic acid and 16.6 g (239 mmol) of hydroxylamine hydrochloride were dissolved in 200 ml of ethanol, then 12.9 g (239 mmol) of sodium methoxide added and heating and refluxing carried out for 2 hours. The reaction liquid was then cooled and concentrated with an evaporator. 60 ml of 5% aqueous sodium hydroxide solution was added to the residue and the insoluble material filtered off. The mother liquor was acidified with concentrated hydrochloric acid, and the precipitate then filtered off and dried. 60 ml of acetic anhydride was added thereto and stirring carried out for 1.5 hours at 100° C. 400 ml of water was added to the reaction liquid and steam distillation performed. The distilled fraction was extracted with dichloromethane, then this dried with anhydrous sodium sulphate, filtered and concentrated. The residue was distilled and 3.83 g (28.3 mmol) of 2-{2-(4,5-dimethylfuran)}acetonitrile obtained.

35 ml of 10% aqueous sodium hydroxide solution was added to the 3.83 g (28.3 mmol) of 2-{2-(4,5-dimethylfuran)}acetonitrile, and stirring carried out for 4 hours at 100° C. The reaction liquid was then cooled and extracted with ethyl acetate. The aqueous layer was acidified with concentrated hydrochloric acid and extracted with ethyl acetate, after which drying, filtering and concentration were performed and 3.80 g (24.6 mmol) of 4,5-dimethyl-2-furanacetic acid was obtained.

1.50 g (9.73 mmol) of the 4,5-dimethyl-2-furanacetic acid, 1.22 g (9.67 mmol) of 4-hydroxy-6-methyl-2-pyrone and 2.22 g (10.7 mmol) of DCC were suspended in 30 ml of chloroform, then 244 mg (2.0 mmol) of DMAP added and stirring carried out overnight at 60° C. The reaction liquid was cooled to room temperature and the insoluble material filtered off. The mother liquor was then concentrated and the residue purified by column chromatography. The solid obtained was recrystallized from diethyl ether, and Compound 7 (488 mg, 186 mmol, 19%) obtained. This was converted to the sodium salt with an equivalent quantity of sodium hydrogen carbonate.

Compound 7
Melting point 116–118° C.
Elemental analysis
　Compositional formula $C_{14}H_{14}O_5$
　Calculated C, 64.12; H, 5.38
　Measured C, 64.06; H, 5.42
$^1$H-NMR (300 MHz, CDCl$_3$) δ=1.92 (s, 3H), 2.18 (s, 3H), 2.28 (s, 3H), 4.36 (s, 2H), 5.95 (s, 1H), 6.04 (s, 1H)
IR (KBr) cm$^{-1}$ 1717, 1653, 1562, 1458, 996, 563
Mass (EI) 262 (M$^+$)

Example 8

Synthesis of Compound 8: 3-{2-(4,5-dimethylfuran-2-yl)}acetyl-4-hydroxy-coumarin

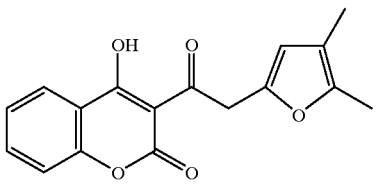

1.50 g (9.73 mmol) of 4,5-dimethyl-2-furanacetic acid, 1.57 g (9.68 mmol) of 4-hydroxycoumarin and 2.27 g (11.0 mmol) of DCC were suspended in 30 ml of chloroform, then 244 mg (2.0 mmol) of DMAP added and stirring carried out overnight at 60° C. The reaction liquid was cooled to room temperature and the insoluble material filtered off. The mother liquid was concentrated and the residue purified by column chromatography. The solid obtained was recrystallized from ethanol, and Compound 8 (466 mg, 1.56 mmol, 16%) was obtained. This was converted to the sodium salt with the equivalent amount of sodium hydrogen carbonate.

Compound 8
Melting point 142–144° C.
Elemental analysis
　Compositional formula $C_{17}H_{14}O_5$
　Calculated C, 68.45; H, 4.73
　Measured C, 68.23; H, 4.76
$^1$H-NMR (300 MHz, CDCl$_3$) δ=1.93 (s, 3H), 2.20 (s, 3H), 4.49 (s, 2H), 6.08 (s, 1H), 7.31–7.38 (m, 2H), 7.714 (t, 1H, J=7.32), 8.06 (d, 1H, J=7.32), 17.18 (s, 1H)
IR (KBr) cm$^{-1}$ 1727, 1618, 1547, 982, 754
Mass (EI) 298 (M$^+$)

Example 9

Synthesis of Compound 9: 3-{(2-furan-2-yl)}acetyl-4-hydroxy-coumarin

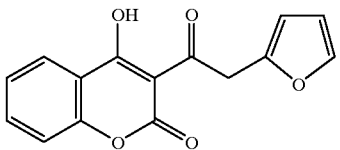

150 ml of acetic acid was added to 18.4 g of manganese (II) acetate and, while stirring at 80° C., 3.0 g of potassium permanganate was added and then stirring conducted for 30 minutes. 27 ml of acetic anhydride was added dropwise and the mixture cooled to room temperature. 7.0 ml of triethyl methanetricarboxylate, 24 ml of furan and 4.9 g of sodium acetate were added, and stirring carried out for 24 hours at 60° C. After cooling the reaction liquid, 80 ml of water was added and extraction performed with toluene, followed by washing with water. The organic layer was dried and concentrated, and the residue purified by column chromatography. 9.1 g (30.5 mmol) of the furanmethanetricarboxylate ester obtained.

110 ml of 1 N aqueous sodium hydroxide solution was added to 9.1 g (30.5 mmol) of the furanmethanetricarboxylate ester of furan, and stirring carried out overnight at 60° C. After acidifying the reaction liquid with concentrated hydrochloric acid, stirring was carried out for 1 hour at 60° C. and then it was cooled. The reaction liquid was extracted with ethyl acetate, and by drying and concentrating there was obtained 1.61 g (12.8 mmol) of furanacetic acid.

1.55 g (12.3 mmol) of the furanacetic acid, 1.99 g (12.3 mmol) of 4-hydroxycoumarin and 2.83 g (13.7 mmol) of DCC were suspended in 50 ml of toluene, then 149 mg (1.22 mmol) of DMAP added and stirring carried out overnight at 60° C. The reaction liquid was then cooled to room temperature and the insoluble material filtered off. The mother liquor was concentrated and the residue purified by column chromatography. The solid obtained was recrystallized from methanol and Compound 9. (594 mg, 2.20 mmol, 18%) obtained. This was converted to the sodium salt with an equivalent amount of sodium hydrogen carbonate.

Compound 9
Melting point 118–120° C.
Elemental analysis
  Compositional formula $C_{15}H_{10}O_5$
  Calculated C, 66.67; H, 3.73
  Measured C, 66.61; H, 3.74
$^1$H-NMR (300 MHz, CDCl$_3$) δ=4.60 (s, 2H), 6.31 (m, 1H), 6.38 (m, 1H), 7.31–7.43 (m, 2H), 7.72 (m, 1H), 8.07 (dd, 1H, J=1.54, 7.69), 17.08 (s, 1H)
IR (KBr) cm$^{-1}$ 1717, 1618, 1551, 1491, 1417, 1238, 988, 746
Mass (EI) 270 (M$^+$)

Example 10

Synthesis of Compound 10: 3-{2-(3-n-propylthiophene-2-yl)}acetyl-4-hydroxy-6-methyl-pyrone

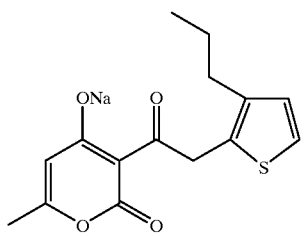

28.0 ml of phosphorus oxychloride was added dropwise to 23.0 ml of DMF, and stirring carried out for 1 hour. To this, 25.0 g (198 mmol) of 3-propylthiophene was added dropwise and then stirring carried out for 1 hour at 100° C. After cooling to room temperature, the reaction mixture was poured into ice-cooled aqueous sodium hydroxide solution, and extraction carried out with dichloromethane. After drying, concentration was performed and purification carried out by column chromatography. 30.5 g (100%) of the 3- and 4-propylthiophene-2-aldehydes was obtained. The ratio of the 3-propyl and 4-propyl forms at this time was about 3:1.

The aldehyde mixture thus obtained was dissolved in 120 ml of THF, then 21.0 ml of methyl methylsulphinylmethyl sulphide and 16.0 ml of Triton B added, and refluxing carried out for 5 hours. The reaction mixture was cooled to room temperature, and concentration performed. The residue was dissolved in dichloromethane and neutralized with dilute sulphuric acid. After drying, concentration was carried out, then 275 ml of 1 N HCl/ethanol added to the residue and refluxing carried out for 5 hours. After cooling to room temperature, concentration was carried out and the residue purified by column chromatography. 42.1 g (100%) of the ethyl 3- and 4-propylthiophene-2-acetates was obtained.

120 ml of 10% aqueous sodium hydroxide solution was added to the ester obtained, and stirring carried out at 60° C. overnight. After cooling to room temperature, the organic material was eliminated with ether, and the aqueous layer was neutralized with concentrated hydrochloric acid. Extraction was performed with dichloromethane and, after drying and concentrating, 32.0 g (173 mmol, 87%) of the 3- and 4-propylthiophene-2-acetic acids was obtained.

The 32.0 g (173 mmol) of the 3- and 4-propylthiophene-2-acetic acids, 21.8 g (173 mmol) of 4-hydroxy-6-methyl-2-pyrone and 39.4 g (191 mmol) of DCC were suspended in 400 ml of chloroform and stirred for 4 hours at room temperature, after which 2.1 g (17.2 mmol) of DMAP was added and stirring carried out overnight at 60° C. Next, the reaction liquid was cooled to room temperature and the insoluble material filtered off. The mother liquor was concentrated and the residue purified by column chromatography. In aqueous methanol solution, conversion was performed to the sodium salt with 11.0 g of sodium hydrogen carbonate, and then this dissolved in water and the organic material extracted with ethyl acetate. Next, the aqueous layer was neutralized with concentrated hydrochloric acid and extracted with dichloromethane. After drying and concentrating, the residue was again purified on a column. 17.8 g (60.8 mmol, 35%) of the 3- and 4-propylthiopheneacetic acid adducts was obtained as an oily material. The 3- and 4-propyl ratio at this time was about 4:1. The sodium salt was formed with an equivalent amount of sodium hydrogen carbonate and, when recrystallization was carried out from isopropyl alcohol, the 3- and 4- propyl ratio was about 10:1. This was taken as Compound 10.

Compound 10
Elemental analysis
  Compositional formula $C_{15}H_{15}NaO_4S$
  Calculated C, 57.32; H, 4.81
  Measured C, 57.10; H, 4.95

Example 11

Synthesis of Compound 11: 3-{2-(3-ethylthiophene-2-yl)}acetyl-4-hydroxy-6-methyl-pyrone

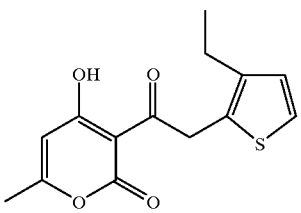

31.5 ml of phosphorus oxychloride was added dropwise to 26.0 ml of DMF and stirring carried out for 1 hour. 25.0 g (223 mmol) of 3-ethylthiophene was added dropwise thereto and, after stirring for 1 hour, stirring was conducted at 100° C. for 1 hour. After cooling to room temperature, dilution was carried out with dichloromethane and the mixture poured into saturated bicarbonate of soda solution and neutralization performed with aqueous sodium hydroxide solution. Extraction was then carried out with dichloromethane, followed by drying and concentrating. The residue was distilled and 25.7 g (183 mmol, 0.1 mmHg, 48–49° C). of an approximately 3:1 mixture of 3-ethylthiophenealdehyde and 4-ethylthiophenealdehyde was obtained as a colourless liquid.

The 25.7 g (183 mmol) of aldehyde was dissolved in 100 ml of THF, then 19.0 ml of methyl methylsulphinylmethyl sulphide and 14.0 ml of Triton B were added, and refluxing performed for 6 hours. The reaction liquid was cooled to room temperature and concentrated. The residue was dissolved in dichloromethane and neutralized with dilute sulphuric acid. After drying, concentration was carried out and the residue purified by column chromatography. To this (40.1 g), there was added 220 ml of 1 N HCl/ethanol and refluxing carried out for 6 hours. After cooling to room temperature, concentration was performed and the residue purified by column chromatography. 29.1 g (146 mmol, 80%) of the ethyl 3- and 4-ethylthiophene-2-acetates was obtained.

90 ml of 10% aqueous sodium hydroxide solution was added to the ethyl ester obtained, and stirring carried out overnight at 90° C. The reaction liquid was then cooled to room temperature, after which the organic material was eliminated with ether. The aqueous layer was neutralized with concentrated hydrochloric acid and extracted with dichloromethane. After drying, concentration was carried out and 25.0 g (146 mmol, 100%) of the 3- and 4-ethylthiophene-2-acetic acids was obtained.

The 25.0 g (146 mmol) of the 3- and 4-ethylthiophene-2-acetic acids, 18.4 g (146 mmol) of 4-hydroxy-6-methyl-2-pyrone and 33.5 g (162 mmol) of DCC were suspended in 400 ml of chloroform, and stirred for 1 hour at room temperature, after which 1.80 g (14.7 mmol) of DMAP was added and stirring carried out overnight at 60° C. Next, the reaction liquid was cooled to room temperature and the insoluble material filtered off. The mother liquor was concentrated and the residue purified by column chromatography. In aqueous methanol solution, conversion was performed to the sodium salt with 8.0 g of sodium hydrogen carbonate, and concentration performed. The residue was dissolved in water, the organic material extracted with diethyl ether, and the aqueous layer concentrated. When the residue was recrystallized from ethanol, the 3- and 4-ethyl ratio was about 20:1. This was taken as Compound 10.
Compound 11
Elemental analysis
Compositional formula $C_{14}H_{14}O_4SNa$
Calculated C, 55.99; H, 4.36
Measured C, 55.84; H, 4.49
$^1$H-NMR (300 MHz, $CD_3OD$) δ= 1.17 (t, 3H, J=7.41), 2.11 (d, 3H, J=0.82), 2.60 (q, 2H, J=7.41), 4.41 (s,2H), 5.69 (d, 1H, J=0.82), 6.85 (d, 1H, J=5.21), 7.09 (d, 1H, J=5.21)

Example 12

Synthesis of Compound 12: 3-{2-(3,5-dimethylthiophene-2-yl)}acetyl-4-hydroxy-6-methyl-pyrone

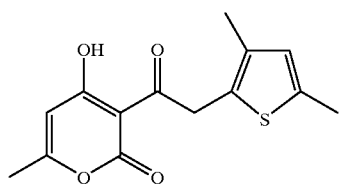

A mixture of 12 ml of N-methylpiperidine and 300 ml of THF was cooled to −78° C. and then 40 ml of 2.5 M butyllithium hexane solution added dropwise, after which 9.6 ml (90 mmol) of 3-methylthiophenealdehyde was added. A further 72 ml of 2.5 M butyllithium hexane solution was added dropwise and stirring carried out for 3 hours at −23° C. Once again, the temperature was returned to −78° C. and 23 ml of methyl iodide added, then the temperature raised to room temperature and stirring carried out for 30 minutes. The reaction liquid was poured into ice water and extracted with ether. After drying, filtering and concentrating, the residue was purified by column chromatography and 12.3 g (87.7 mmol) of 3,5-dimethylthiophene-2-aldehyde obtained.

A mixture of the 12.3 g (87.7 mmol) of 3,5-dimethylthiophene-2-aldehyde, 70 ml of acetic acid, 11.5 g (86.3 mmol) of rhodanine and 19.3 g (241 mmol) of sodium acetate was stirred for 1.5 hours at 100° C. Ice water was added to the reaction liquid and filtering and washing with water performed. 200 ml of 10% aqueous sodium hydroxide solution was added to the solid obtained and stirring carried out for 3 hours at 100° C. Next, the reaction liquid was cooled, then acidified with concentrated hydrochloric acid and the precipitate which was deposited was filtered off and washed with water. Drying was carried out using a vacuum pump and there was obtained 9.42 g (43.9 mmol) of the thiopyruvic acid.

The 9.42 g (43.9 mmol) of the thiopyruvic acid and 9.16 g (131 mmol) of hydroxylamine hydrochloride were dissolved in 200 ml of ethanol, then 7.10 g (131 mmol) of sodium methoxide added and heating and refluxing carried out for 4 hours. The reaction liquid was cooled and then concentrated using an evaporator. 50 ml of 5% aqueous sodium hydroxide solution was added to the residue and the insoluble material filtered off. The mother liquid was acidified with concentrated hydrochloric acid, and then the precipitate filtered off and dried. 70 ml of acetic anhydride was added thereto, and stirring carried out for 1.5 hours at 100° C. 400 ml of water was added to the reaction liquid and steam distillation performed. The distilled fraction was extracted with dichloromethane and then this dried with anhydrous sodium sulphate, filtered and concentrated. The residue was distilled (0.08 mmHg, 65° C.), and 4.00 g (26.4 mmol) of 3,5-dimethylthiopheneacetonitrile obtained.

30 ml of 10% aqueous sodium hydroxide solution was added to the 4.00 g (26.4 mmol) of 3,5-dimethylthiopheneacetonitrile and stirring carried out for 5 hours at 100° C. The reaction liquid was cooled and extracted with ethyl acetate. The aqueous layer was acidified with concentrated hydrochloric acid and extracted with ethyl acetate, after which drying, filtering and concentration were conducted, and 3.82 g (22.4 mmol) of 3,5-dimethylthiopheneacetic acid was obtained.

The 3.82 g (22.4 mmol) of 3,5-dimethylthiopheneacetic acid, 2.87 g (22.7 mmol) of 4-hydroxy-6-methyl-2-pyrone and 5.13 g (24.8 mmol) of DCC were suspended in 70 ml of toluene, then 273 mg (2.23 mmol) of DMAP added and stirring carried out overnight at 90° C. The reaction liquid was cooled to room temperature and the insoluble material filtered off. The mother liquor was concentrated and the residue purified by column chromatography. The solid obtained was recrystallized from ethanol and Compound 12 (684 mg, 2.45 mmol, 11%) obtained. This was converted to the sodium salt with an equivalent quantity of sodium hydrogen carbonate.

Compound 12

Melting point 114–116° C.

Elemental analysis

Compositional formula $C_{14}H_{14}O_4S$

Calculated C, 60.42; H, 5.07; S, 11.52

Measured C, 60.42; H, 5.14; S, 11.48

$^1$H-NMR (300 MHz, CDCl$_3$) δ=2.09 (s, 3H), 2.29 (d, 3H, J=0.77), 2.41 (s, 3H), 4.46 (s, 2H), 5.96 (d, 1H, J=0.77), 6.52 (s, 1H), 16.26 (s, 1H)

IR (KBr) cm$^{-1}$ 1725, 1642, 1624, 1560, 1421, 996, 938, 843

Mass (EI) 278 (M$^+$)

Example 13

Synthesis of Compound 13: 3-{2-(5-acetylfuran-2-yl)}acetyl-4-hydroxy-6-methyl-pyrone

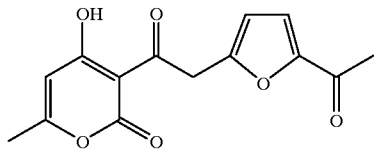

30 ml of 10% aqueous sodium hydroxide solution and 50 ml of methanol were added to 6.40 g (18.8 mmol) of 5-acetylfuran-2-methanetricarboxylate ester, and stirring carried out for 4 hours at 70° C. The reaction liquid was cooled to room temperature and concentrated. The residue was dissolved in water and neutralized with concentrated hydrochloric acid, after which it was extracted with dichloromethane. By drying and concentrating, 2.49 g (14.8 mmol) of 5-acetyl-2-furanacetic acid was obtained.

The 2.49 g (14.8 mmol) of 5-acetyl-2-furanacetic acid, 1.87 g (14.8 mmol) of 4-hydroxy-6-methyl-2-pyrone and 3.37 g (16.3 mmol) of DCC were suspended in 25 ml of chloroform, then 183 mg (1.50 mmol) of DMAP added and stirring carried out overnight at 60° C. The reaction liquid was cooled to room temperature and the insoluble material filtered off. The mother liquor was concentrated and the residue purified by column chromatography. The solid obtained was recrystallized from ethanol and Compound 13 (496 mg, 1.79 mmol, 12%) obtained. This was converted to the sodium salt with an equivalent quantity of sodium hydrogen carbonate.

Compound 13

Melting point 135–137° C.

Elemental analysis

Compositional formula $C_{14}H_{12}O_6$

Calculated C, 60.87; H, 4.38

Measured C, 61.03; H, 4.39

$^1$H-NMR (300 MHz, CDCl$_3$) δ=0.31 (d, 3H, J =0.82), 2.45 (s, 3H), 4.55 (s, 2H), 5.99 (d, 1H), J 0.82), 6.43 (dd, 1H, J=0.55, 3.57), 7.16 (d, 1H, J=3.29), 15.79 (s, 1H)

IR (KBr) cm$^{-1}$ 1721, 1671, 1644, 1574, 1514

Mass (EI) 276 (M$^+$)

Example 14

Synthesis of Compound 14: 3-{2-(3-methylfuran)}acetyl-4-hydroxy-6-methyl-pyrone

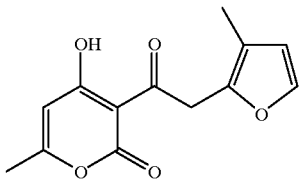

13.5 ml of phosphorus oxychloride was added dropwise to 13.0 ml of DMF and stirring carried out for 1 hour. The reaction liquid was ice-cooled and 10.3 g (125 mmol) of 3-methylfuran added dropwise. After stirring for 1 hour, stirring was then conducted at 40° C. for 30 minutes, and the mixture poured into water. After neutralizing with aqueous sodium carbonate solution, extraction was carried out with ether, followed by drying, filtering and concentrating. The residue was distilled and 7.05 g (64 mmol) of an approximately 15:1 mixture of 3-methylfuranaldehyde and 4-methylfuranaldehyde was obtained as a colourless liquid.

A mixture of the 7.05 g (64 mmol) of aldehyde, 60 ml of acetic acid, 8.52 g (63.4 mmol) of rhodanine and 14.7 g (179 mmol) of sodium acetate was stirred for 1.5 hours at 100° C. Ice water was added to the reaction liquid, and filtering and washing with water performed. 200 ml of 10% aqueous sodium hydroxide solution was added to the solid obtained and stirring carried out for 2 hours at 100° C. The reaction liquid was cooled, acidified with concentrated hydrochloric acid and the deposited precipitate filtered off and washed with water. Drying was performed using a vacuum pump and 7.99 g (43.4 mmol) of the thiopyruvic acid obtained.

The 7.99 g (43.4 mmol) of this thiopyruvic acid and 9.05 g (130 mmol) of hydroxylamine hydrochloride were dissolved in 150 ml of ethanol, then 7.03 g (130 mmol) of sodium methoxide added and heating and refluxing carried out for 2 hours. The reaction liquid was cooled and then concentrated using an evaporator. 50 ml of 5% aqueous sodium hydroxide solution was added to the residue and the insoluble material filtered off. The mother liquid was acidified with concentrated hydrochloric acid, and then the precipitate filtered off and dried. 70 ml of acetic anhydride was added thereto, and stirring carried out for 2 hours at 100° C. 400 ml of water was added to the reaction liquid and steam distillation performed. The distilled fraction was extracted with dichloromethane and then dried with anhydrous sodium sulphate, filtered and concentrated, and 2.03 g (16.7 mmol) of a mixture of the 3- and 4-methylfuranacetonitiles obtained. 30 ml of 10% aqueous sodium hydroxide solution was added thereto and stirring carried out for 4 hours at 90° C. The reaction liquid was cooled and extracted with ethyl acetate. The aqueous layer was acidified with concentrated hydrochloric acid and extracted with ethyl acetate, after which drying filtering and concentration were carried out and 1.61 g (11.5 mmol) of the 3- and 4-methylfuranacetic acids obtained.

The 1.61 g (11.5 mmol) of the 3- and 4-methylfuranacetic acids, 1.45 g (11.5 mmol) of 4-hydroxy-6-methyl-2-pyrone and 2.65 g (12.8 mmol) of DCC were suspended in 50 ml of toluene, then 125 mg (1.02 mmol) of DMAP added and stirring carried out overnight at 70° C. The reaction liquid was cooled to room temperature and the insoluble material filtered off. The mother liquor was concentrated and the residue purified by column chromatography. The solid obtained was recrystallized from ethanol and Compound 14

(1.17 g, 4.73 mmol, 41%) obtained. This was converted to the sodium salt with an equivalent quantity of sodium hydrogen carbonate.

Compound 14
Melting point 116–116° C.
Elemental analysis
Compositional formula $C_{13}H_{12}O_5$
Calculated C, 62.90; H, 4.87
Measured C, 62.89; H, 4.89
$^1$H-NMR (300 MHz, CDCl$_3$) δ=0.31 (d, 3H, J=0.82), 2.45 (s, 3H), 4.55 (s, 2H), 5.99 (d, 1H, J=0.82), 6.43 (dd, 1H, J=0.55, 3.57), 7.16 (d, 1H, J=3.29), 15.79 (s, 1H)
IR (KBr) cm$^{-1}$ 1716, 1648, 1560, 1458, 1088, 994, 932, 858, 741, 726
Mass (EI) 248 (M$^+$)

Example 15
Synthesis of Compound 15: 3-{2-(benzofuran-2-yl)}acetyl-4-hydroxy-6-methyl-pyrone

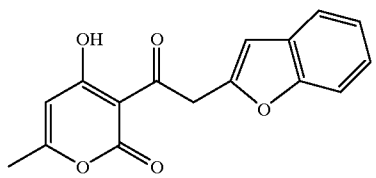

A mixture of 10.3 g (70.9 mmol) of 2-benzofuranaldehyde, 60 ml of acetic acid, 9.43 g (70.8 mmol) of rhodanine and 17.1 g (208 mmol) of sodium acetate was stirred for 1.5 hours at 100° C. Water was added to the reaction liquid and then filtering performed followed by washing with water. 200 ml of 10% aqueous sodium hydroxide solution was added to the solid obtained and stirring carried out for 30 minutes at 100° C. After cooling the reaction liquid, it was acidified with concentrated hydrochloric acid, then the precipitate which was deposited was filtered off and washed with water. The solid obtained was dried using a vacuum pump and 15.0 g (about 67.9 mmol) of 3-(2-benzofurano)thiopyruvic acid was obtained.

200 ml of sodium ethoxide/ethanol solution (sodium 4.6 g) was prepared, then 14.1 g (203 mmol) of hydroxylamine hydrochloride and 15.0 g (about 67.9 mmol) of the thiopyruvic acid derivative added, and heating and refluxing carried out for 4 hours. The reaction liquid was then cooled and concentrated using an evaporator. 60 ml of 5% aqueous sodium hydroxide solution was added to the residue but it largely remained undissolved. Thus, the mixture was acidified as it was with concentrated hydrochloric acid and then filtering, washing with water and drying carried out. 60 ml of acetic anhydride was added thereto and stirring carried out for 1.5 hours at 100° C. Next, 400 ml of water was added to the reaction liquid and steam distillation performed. Since the target material essentially did not distil over, the distillation was halted and the aqueous layer extracted with ethyl acetate. This was then thoroughly neutralized with aqueous sodium hydrogen carbonate solution and drying, filtering and concentration performed. The residue was purified by column chromatography and 7.91 g (50.3 mmol) of 3-(2-benzofurano)acetonitrile obtained.

40 ml of 10% aqueous sodium hydroxide solution was added to the 7.91 g (50.3 mmol) of the acetonitrile derivative and stirring carried out for 4 hours at 100° C. The reaction liquid was cooled and then extracted with dichloromethane. The aqueous layer was acidified with concentrated hydrochloric acid and extracted with dichloromethane, after which drying, filtering and concentration were conducted, and 7.81 g (mmol) of 2-benzofuranacetic acid was obtained.

1.76 g (10.0 mmol) of the 2-benzofuranacetic acid, 1.26 g (10.0 mmol) of 4-hydroxy-6-methyl-2-pyrone and 2.27 g (11.1 mmol) of DCC were suspended in 50 ml of chloroform, then 130 mg (1.06 mmol) of DMAP added and stirring carried out overnight at 60° C. The reaction liquid was cooled to room temperature and the insoluble material filtered off. The mother liquor was concentrated and the residue purified by column chromatography. The solid obtained was recrystallized from ethanol and Compound 15 (614 mg, 2.16 mmol, 21%) obtained. This was converted to the sodium salt with an equivalent quantity of sodium hydrogen carbonate.

Compound 15
Melting point 127–129° C.
Elemental analysis
Compositional formula $C_{16}H_{12}O_5$
Calculated C, 67.60; H, 4.25
Measured C, 68.24; H, 4.30
$^1$H-NMR (300 MHz, CDCl$_3$) δ=2.30 (d, 3H, J=0.73), 4.61 (d, 2H, J=0.73), 5.98 (d, 1H, J=0.73), 6.68 (d, 1H, J=0.73), 7.19–7.27 (m, 2H), 7.45 (dd, 1H, J=1.10, 6.95), 7.52 (m, 1H), 15.98 (s, 1H)
IR (KBr) cm$^{-1}$ 1717, 1649, 1562, 1465
Mass (EI) 284 (M$^+$)

Example 16
Synthesis of Compound 16: 3-{2-(benzofuran-2-yl)}acetyl-4-hydroxy-coumarin

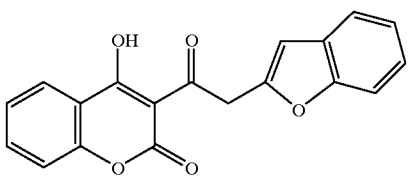

1.76 g (10.0 mmol) of 2-benzofuranacetic acid, 1.62 g (10.0 mmol) of 4-hydroxy-coumarin and 2.27 g (11.1 mmol) of DCC were suspended in 50 ml of chloroform, then 130 mg (1.06 mmol) of DMAP added and stirring carried out overnight at 60° C. The reaction liquid was then cooled to room temperature and the insoluble material filtered off. The mother liquor was concentrated and the residue purified by column chromatography. The solid obtained was recrystallized from ethanol and Compound 16 (460 mg, 1.43 mmol, 14%) obtained. This was converted to the sodium salt with an equivalent quantity of sodium hydrogen carbonate.

Compound 16
Melting point 147–148° C.
Elemental analysis
Compositional formula $C_{19}H_{12}O_5$
Calculated C, 71.25; H, 3.78
Measured C, 71.23; H, 3.90
$^1$H-NMR (300 MHz, CDCl$_3$) δ=4.74 (s, 2H), 6.71 (d, 1H, J=0.73), 7.20–7.28 (m, 2H), 7.32–7.38 (m, 2H), 7.46 (dd, 1H, J=1.10, 8.05), 7.54 (m, 1H), 7.72 (m, 1H), 8.07 (dd, 1H, J=1.83, 8.05)
IR (KBr) cm$^{-1}$ 1719, 1618, 1551, 1454, 1257, 762, 750
Mass (EI) 320 (M$^+$)

Example 17

Synthesis of Compound 17: 3-{2-(4-methylthiophene-2-yl)}acetyl-4-hydroxy-6-methyl-pyrone

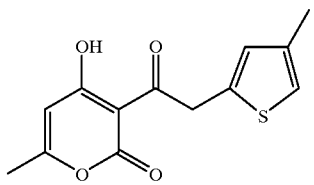

150 ml of acetic acid was added to 18.4 g of manganese (II) acetate and, while stirring at 80° C., 3.0 g of potassium permanganate was added and then stirring conducted for 30 minutes. 27 ml of acetic anhydride was added dropwise, after which the mixture was cooled to room temperature. 7.0 ml of ethyl methanetricarboxylate, 33 mmol of 3-methylthiophene and 4.92 g of sodium acetate were added, and stirring carried out overnight at 60° C. After cooling the reaction liquid, 100 ml of water was added and extraction performed with toluene. The toluene layer was dried, filtered and concentrated, and the residue purified by column chromatography. 5.66 g of product was obtained. When NMR identification was carried out, this was found to be a mixture of the 4-methylthiophene-2-methanetricarboxylate ethyl ester and the 3-methylthiophene-2-methanetricarboxylate ethyl ester in roughly 2:1 proportions.

50 ml of 10% aqueous sodium hydroxide solution was added to the 5.66 g of thiophenemethanetricarboxylate ester (mixture) and stirring carried out for 2 days at 60° C. to 70° C. The reaction liquid was then acidified by the addition of concentrated hydrochloric acid and stirring carried out for 1 hour at 70° C. to effect decarboxylation. The reaction liquid was then cooled to room temperature and extracted with dichloromethane. The dichloromethane layer was dried, filtered and concentrated, and 2.21 g of the 3- and 4-methylthiopheneacetic acids obtained.

1.79 g of pyrone, 3.22 g of DCC, 50 ml of chloroform and 170 mg of DMAP were added to the 2.21 g of the 3- and 4-methylthiopheneacetic acids, and stirring carried out for 2 days at 60° C. The reaction liquid was then cooled to room temperature, filtered and the filtrate concentrated. The residue was purified by column chromatography with dichloromethane, and an oily material obtained. Ethanol was added to the oily material obtained and, on leaving in a refrigerator, crystals were deposited. The deposited crystals were filtered off and 754 mg obtained. When identification was carried out by NMR, it was found that practically only the 4-methyl derivative had been obtained. This was converted to the sodium salt with an equivalent quantity of sodium hydrogen carbonate.

Compound 17

Melting point 110–114° C.

Elemental analysis

Compositional formula $C_{13}H_{12}O_4S$

Calculated C, 59.08; H, 4.58; S, 12.13

Measured C, 58.99; H, 4.55

$^1$H-NMR (300 MHz, CDCl$_3$) δ=2.22 (d, 3H, J=0.77), 2.29 (d, 3H, J=0.77), 4.57 (d, 2H, J=0.77), 5.96 (d, 1H, J=0.77), 6.81 (m, 2H), 16.21 (s, 1H)

IR (KBr) cm$^{-1}$ 1707, 1647, 1554, 1458, 994

Mass (EI) 264 (M$^+$)

Example 18

Synthesis of Compound 18: 3-{2-(5-tert-butylfuran-2-yl)}acetyl-4-hydroxy-6-methylpyrone

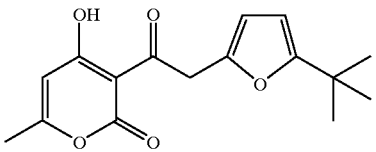

150 ml of acetic acid was added to 18.4 g of manganese (II) acetate and, while stirring at 80° C., 3.0 g of potassium permanganate was added and then stirring conducted for 30 minutes. 27 ml of acetic anhydride was added dropwise, after which the mixture was cooled to room temperature. 7.0 ml of ethyl methanetricarboxylate, 4.7 ml of 5-tert-butylfuran and 4.92 g of sodium acetate were added, and stirring carried out overnight at 60° C. After cooling the reaction liquid, 100 ml of water was added and extraction performed with toluene. The toluene layer was dried, filtered and concentrated, and the residue purified by column chromatography. 11.2 g of the furanmethanetricarboxylate ester was obtained.

80 ml of 10% aqueous sodium hydroxide solution was added to the 11.2 g of the furanmethanetricarboxylate ester obtained and stirring carried out for 5 days at 60° C. to 70° C. The reaction liquid was then acidified by the addition of concentrated hydrochloric acid and stirring carried out for 1 hour at 70° C. to effect decarboxylation. The reaction liquid was then cooled to room temperature and extracted with dichloromethane. The dichloromethane layer was dried, filtered and concentrated, and 5.46 g of 5-tert-butylfuranacetic acid obtained.

3.77 g of the pyrone, 6.78 g of DCC, 100 ml of chloroform and 365 mg of DMAP were added to the 5.46 g of 5-tert-butylfuranacetic acid, and stirring carried out overnight at 60° C. The reaction liquid was cooled to room temperature, then filtered and the filtrate concentrated. The residue was passed through a chromatographic column with dichloromethane and an oily material obtained. Ethanol was added to the oily material obtained and, on leaving in a refrigerator, crystals were deposited. The deposited crystals were filtered off and 2.21 g of the target material obtained. This was converted to the sodium salt with an equivalent quantity of sodium hydrogen carbonate.

Compound 18

Melting point 90–91° C.

Elemental analysis

Compositional formula $C_{16}H_{18}O_5$

Calculated C, 66.19; H, 6.25

Measured C, 66.16; H, 6.26

$^1$H-NMR (300 MHz, CDCl$_3$) δ=1.26 (s, 9H), 2.28 (d, 3H, J=0.77), 4.42 (s, 2H), 5.90 (d, 1H, J=3.07), 5.96 (d, 1H, J=0.77), 6.13 (m, 1H), 16.23 (s, 1H)

IR (KBr) cm$^{-1}$ 2972, 1719, 1649, 1560, 1452, 993

Mass (EI) 290 (M$^+$)

Example 19
Synthesis of Compound 19: 3-{2-(3-methoxythiophen-2-yl)}acetyl-4-hydroxy-6-methyl-pyrone

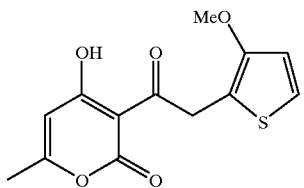

While stirring 100 ml of ether at −40° C., 40 ml of 2.5 M n-butyllithium/hexane solution was added and then 10.0 g (87.6 mmol) of 3-methoxythiophene added dropwise. Following the dropwise addition, the temperature was raised to 0° C. and stirring carried out for 30 minutes. After re-cooling to −60° C., 7.5 ml of DMF was added dropwise and stirring carried out for 1 hour. The reaction liquid was poured into dilute hydrochloric acid and extracted with ethyl acetate. After drying and concentrating, the residue was recrystallized from ethyl acetate hexane, and 8.93 g (62.8 mmol, 72%) of yellow crystals of the 3-methoxy-2-thiophenealdehyde obtained 60 ml of acetic acid was added to 8.88 g (62.4 mmol) of the 3-methoxy-2-thiophenealdehyde, 8.30 g (62.3 mmol) of rhodanine and 14.4 g of sodium acetate, and stirring carried out for hours at 100° C. The reaction liquid was cooled, water added and the precipitate filtered off. 100 ml of 10% aqueous sodium hydroxide solution was added to the powder obtained and stirring carried out for 2 hours at 100° C. The reaction liquid was cooled and the organic material extracted with ether. The aqueous layer was neutralized with hydrochloric acid and the precipitate filtered off, washed with water and dried. 9.67 g of the thiolcarboxylic acid was obtained.

9.32 g of hydroxylamine hydrochloride, 100 ml of ethanol and 7.24 g of sodium methoxide were added to the 9.67 g of the thiolcarboxylic acid and heating and refluxing carried out for 2 hours. The reaction liquid was then cooled and concentrated. 40 ml of 10% aqueous sodium hydroxide solution was added to the residue and the insoluble material filtered off. The mother liquor was neutralized with concentrated hydrochloric acid, and extraction performed with ethyl acetate. After drying and concentrating, 50 ml of acetic anhydride was added to the residue and stirring carried for 2 hours at 100° C. Water was added to the reaction liquid and distillation performed. The distilled fraction was extracted with toluene and purified by chromatography. 2.21 g (14.4 mmol, 23%) of the 3-methoxy-2-thiophenacetonitrile was obtained.

10 ml of 10% aqueous sodium hydroxide solution was added to the 2.21 g (14.4 mmol) of the 3-methoxy-2-acetonitrile, and stirring carried out for 6 hours at 90° C. The reaction liquid was then cooled and extracted with ethyl acetate. The aqueous layer was neutralized with hydrochloric acid and extracted with ether, after which drying and concentration were performed. 2.40 g (13.9 mmol, 96%) of 3-methoxy-2-thiopheneacetic acid was obtained.

1.75g of the pyrone, 3.16 g of DCC and 60 ml of toluene were added to the 2.40 g (13.9 mmol) of 3-methoxy-2-thiopheneacetic acid, and stirring carried out overnight at 70° C., after which 180 mg of DMAP was added and stirring carried out for 8 hours at 70° C. The reaction liquid was then cooled, and the insoluble material filtered off. The mother liquor was washed with dilute hydrochloric acid, then dried and concentrated, after which purification was performed by chromatography and recrystallization conducted from ethanol. 816 mg (2.91 mmol, 21%) of red needle crystals of the target material was obtained. This was converted to the sodium salt with an equivalent quantity of sodium hydrogen carbonate.

Compound 19
Melting point 104–106° C.
$^1$H-NMR (300 MHz, CDCl$_3$) δ=2.29 (s, 3H), 3.82 (s, 3H), 4.51 (s, 2H), 5.96 (s, 1H), 6.88 (d, 1H, J=5.77), 7.16 (d, 1H, 5.77), 16.19 (s, 1H)
IR (KBr) cm$^{-1}$ 1721, 1646, 1561, 1068, 991
Mass (EI) 280 (M$^+$)

Example 20
Synthesis of Compound 20 3-{2-(3-bromothiophene-2-yl)}acetyl-4-hydroxy-6-methylpyrone

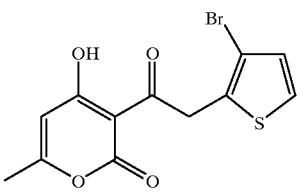

3-Bromothiophene-2-aldehyde (4.9 g, 25.6 mmol) was dissolved in THF (20 ml), then methyl methylsulphinylmethyl sulphide (2.6 ml, 26 mmol) and Triton B (2.5 ml) were added, and heating and refluxing performed for 3 hours. After returning to room temperature, dichloromethane (100 ml) and dilute sulphuric acid were added, then separation/extraction performed, followed by drying with anhydrous sodium sulphate, after which the solvent distilled off.

HCl (0.5 M ethanol solution, 100 ml) was added to the condensate as it was, without purification, and heating and refluxing carried out for 14 hours. The solvent was then distilled off, dichloromethane and dilute hydrochloric acid added and extraction performed, followed by drying with anhydrous sodium sulphate. The solvent was distilled off and purification performed by column chromatography. There was obtained ethyl 3-bromo-2-thiopheneacetate containing a small amount of impurity.

10% aqueous sodium hydroxide solution (100 ml) was added to this ester and stirring carried out for 14 hours at 50° C., after which ether extraction was carried out and unnecessary organic material eliminated. Next, acidification was performed with dilute hydrochloric acid and extraction carried out with dichloromethane. After drying, the solvent was distilled off and there was obtained 3-bromo-2-thiopheneacetic acid (4.7 g).

To a chloroform (40 ml) suspension of 4-hydroxy-6-methyl-2-pyrone (2.1 g, 16.7 mmol) and 3-bromo-2-thiopheneacetic acid (3.6 g, 16.3 mmol), there was added at room temperature dicyclohexylcarbodiimide (3.6 g, 18 mmol). Then, DMAP (0.1 g, 0.8 mmol) was added and heating carried out for 1 hour at 40° C., after which 4-dimethylaminopyridine (0.2 g, 1.6 mmol) was also added and heating and refluxing performed for 6 hours. After returning to room temperature, the dicyclohexylurea was filtered off and the reaction solution washed with dilute hydrochloric acid, following which the aqueous layer was extracted with dichloromethane. After drying with anhydrous sodium sulphate, the solvent was distilled off and separation and purification carried out by column chromatography. When recrystallization was carried out from ethanol, Compound 20 (1.56 g, 30%) was obtained as white crystals.

Compound 20

Melting point 127–128° C.

Elemental analysis

Compositional formula $C_{12}H_9BrO_4S$

Calculated C, 43.79; H, 2.76; Br, 24.27; S, 9.74

Measured C, 43.73; H, 2.71; Br, 24.50; S, 9.70

$^1$H-NMR (300 MHz, CDCl$_3$) δ=2.36 (d, J=0.82 Hz, 3H), 4.64 (s, 2H), 6.24 (q, J=0.82 Hz, 1H), 7.04 (d, J=5.2 Hz, 1H), 7.45 (d, J=5.2 Hz, 2H)

IR (KBr) cm$^{-1}$ 1715, 1649, 1566, 1454, 1319, 1238, 992, 934, 857

Mass (EI) 329 (M$^+$)

Example 21

Synthesis of Compound 21: 3-{2-(3-phenylthiophene-2-yl)}acetyl-4-hydroxy-6-methyl-pyrone

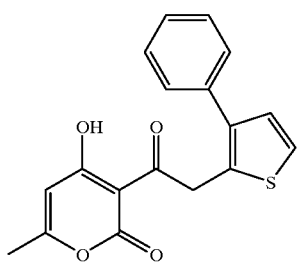

Pd(PPh$_3$)$_4$ (60 mg, 0.05 mmol) and tripotassium phosphate trihydrate (2.0 g, 7.5 mmol) were added to 3-{2-(3-bromothiophene)acetyl}-4-hydroxy-6-methyl-2-pyrone (1.00 g, 2.53 mmol) and the atmosphere replaced by argon. DMF (25 ml) was added and then phenyl-1,3,2-dioxaborinane (0.42 ml, 2.8 mmol), and stirring carried out for 7 hours at 100° C.

After returning to room temperature, dichloromethane and dilute hydrochloric acid were added and separation performed. The organic layer was extracted/washed three times with distilled water. Then, after drying the organic layer with anhydrous sodium sulphate, purification was performed by column chromatography. When recrystallization was performed from ethanol, Compound 21 (502 mg, 61%), in which the 3-position on the thiophene ring was substituted with a phenyl ring, was obtained as pale red crystals.

Compound 21

Melting point 109–110° C.

Elemental analysis

Compositional formula $C_{18}H_{14}O_4S \cdot 0.4H_2O$

Calculated C, 64.81; H, 4.47

Measured C, 64.79; H, 4.14

$^1H^1$-NMR (300 MHz, CD$_3$OD) δ=2.33 (d, J=0.82 Hz, 3H), 4.62 (s, 2H), 6.21 (,J=0.82 Hz, 1H), 7.11 (d, J=5.2 Hz, 1H), 7.38 (d, J=5.2 Hz, 1H), 7.31–7.44 (m, 4H)

IR (KBr) cm$^{-1}$ 1721, 1644, 1564, 1555, 1456, 1011, 994

Mass (EI) 326 (M$^+$)

Example 22

Synthesis of Compound 22: 3-{2-(4-bromothiophene-2-yl)}acetyl-4-hydroxy-6-methyl-pyrone

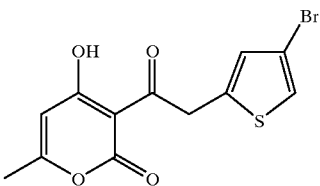

15 ml of THF, 2 ml of Triton B and 2.75 ml of methyl methylthiomethylsulfide were added to 5.00 g (26.2 mmol) of 4-bromo-2-thiophenealdehyde, and heating and refluxing carried out for 7 hours. The reaction liquid was then cooled and purification performed by chromatography. 26 ml of 1 N HCl/ethanol solution was added thereto, and heating and refluxing performed for 6 hours. After cooling the reaction liquid it was concentrated and the residue dissolved in dichloromethane, then washing performed with dilute sulphuric acid. After drying and concentrating, purification was performed by chromatography and 4.94 g (19.8 mmol, 75%) of ethyl 4-bromo-2-thiopheneacetate obtained.

12 ml of 10% aqueous sodium hydroxide solution was added to the 4.94 g (19.8 mmol) of ethyl 4-bromo-2-thiopheneacetate and stirring carried out for 5 hours at 90° C. The reaction liquid was then cooled and extracted with ether. The aqueous layer was neutralized with hydrochloric acid, extracted with ether, then dried and concentrated. 4.24 g (19.1 mmol, 96%) of 4-bromo-2-thiopheneacetic acid was obtained.

2.41g of the pyrone, 4.33 g of DCC and 100 ml of toluene were added to the 4.24 g (19.1 mmol) of 4-bromo-2-thiopheneacetic acid, and stirring carried out overnight at 70° C., after which 234 mg of DMAP was added and stirring carried out for 5 hours at 70° C. The reaction liquid was cooled, and the insoluble material filtered off. The mother liquor was washed with dilute hydrochloric acid, then dried and concentrated, after which purification was performed by chromatography. Recrystallization conducted from ethanol, and 1.28 mg (3.88 mmol, 20%) of red-brown crystals of the target material was obtained.

Compound 22

Melting point133–135° C.

$^1$H-NMR (300 MHz, CDCl$_3$) δ=2.30 (d, 3H, J=0.77), 4.58 (d, 2H, J=0.77), 5.99 (s, 1H), 6.92 (t, 1H, J=0.77), 7.14 (d, 1H, J=1.54), 16.01 (s, 1H)

IR (KBr) cm$^{-1}$ 1705, 1652,1560, 997

Example 23

Synthesis of Compound 23: 3-{2-(3-nitrothiophene-2-yl)acetyl-4-hydroxy-6-methyl-pyrone)

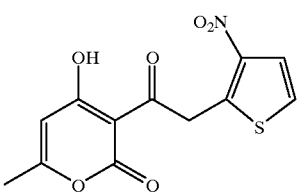

5 ml of acetic anhydride was added, to 2.5 g (10.0 mmol) of 3-(2-thiophene)acetyl-4-hydroxy-6-methyl-2-pyrone and then, while stirring on an ice bath, there was added dropwise a solution formed by adding 0.84 ml of nitric acid to 1.4 ml of acetic anhydride. Following the dropwise addition, stirring was carried out for 2 hours on the ice bath and then water added to the reaction liquid, after which filtering was performed. The solid obtained was subjected to hot filtration with methanol, and the mother liquor purified by chromatography. 749 mg of yellow crystals were obtained. It was confirmed by NMR that this was the compound with the nitro group substituted at the 5-position on the thiophene. Furthermore, the solid which did not dissolve in the hot methanol, was purified by chromatography and recrystalized. 137 mg of colourless crystals were obtained, and these were confirmed as being the compound with the nitro group at the thiophene ring 3-position.

Compound 23
Melting point 199–201° C.
$^1$H-NMR (300 MHz, CDCl$_3$) δ=2.33 (s, 3H), 4.96 (s, 2H), 6.00 (d, 1H, J=0.77), 7.22 (d, 1H, J=5.77), 7.68 (d, 1H, J=5.77), 15.56 (s, 1H)

Example 24
Synthesis of Compound 24: Mixture of 3-{2-(3-methylthiothiophene-2-yl)acetyl-4-hydroxy-6-methyl-pyrone) and 3-{2-(4-methylthiothiophene)acetyl-4-hydroxy-6-methyl-pyrone)

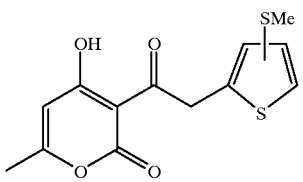

Butyllithium (44 ml of a 2.5 M hexane solution, 0.11 mol) was added to THF (80 ml) at −78° C., and then 3-bromothiophene (9.5 ml, 100 mmol) added dropwise. The temperature rose to −30° C. and it was again cooled to −78° C., then dimethyl disulphide (11 ml, 0.12 mol) added and the temperature increased to −20° C. Distilled water (100 ml) was added and extraction with ether performed, after which drying was carried out with anhydrous magnesium sulphate and the solvent distilled off. The residue was distilled under reduced pressure and when the fraction obtained at 70–80° C. (15 mmHg) was collected, 3-methylthiothiophene was obtained.

Again, butyllithium (24 ml of a 2.5 M hexane solution, 60 mmol) was added to THF (50 ml) at −40° C., and then the 3-methylthiothiophene (7.1 g, 55 mmol) added dropwise. The temperature rose to 0° C. and it was again cooled to −70° C., then DMF (5.0 ml, 65 mmol) added and the temperature increased to −40° C. The contents were added to ice-cooled 2N hydrochloric acid (250 ml) and extraction performed with ether, after which drying was carried out with anhydrous magnesium sulphate and the solvent distilled off. The residue was distilled under reduced pressure and when the fraction obtained at 110–115° C. (1 mmHg) was collected, a mixture of 3-methylthiothiophene-2-aldehyde and 4-methylthiothiophene-2-aldehyde was obtained, and no selectivity was observed.

Using this aldehyde, conversion to the thiopheneacetic acid was investigated via reaction with methyl methylsulphinylmethyl sulphide in the manner described above. Furthermore, when the hydroxypyrone was added and acylation performed, Compound 24 was obtained as a mixture of the two types of positional isomers.

Compound 24
Melting point 97–99° C.
High resolution mass spectrum
 Compositional formula C$_{13}$H$_{12}$O$_4$S$_2$
 Calculated 296.0177
 Measured 296.0184
$^1$H-NMR (300 MHz, CD$_3$OD) δ=3-SMe isomer: 2.36 (d, J=0.82, 3H), 2.37 (s, 3H), 4.71 (s, 2H), 6.23 (q, J=0.82, 1H), 7.13 (d, J=5.2, 1H), 7.39 (d, J=5.2, 1H)
 4-SMe isomer: 2.34 (d, J=0.82 Hz, 3H), 2.47 (s, 3H), 4.58 (s, 2H), 6.22 (q, J=0.82 Hz, 1H), 6.90 (d, J=1.6 Hz, 1H), 7.00 (d, J=1.6 Hz, 1H)
IR (KBr) cm$^{-1}$ 1709, 1651, 1557, 1460, 994, 944
Mass (EI) 296 (M$^+$)

Example 25
Synthesis of Compound 25: 2-2-{2-(2-furan-2-yl)}propionyl-4-hydroxy-6-methyl-pyrone

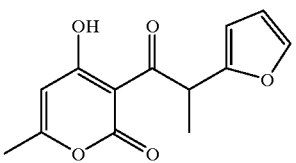

While ice cooling, a tetrahydrofuran (10 ml) solution of 3-(2-furanacetyl-4-hydroxy-6-methyl-2-pyrone (800 mg, 3.42 mmol) was added dropwise to a tetrahydrofuran (15 ml) suspension of sodium hydride (160 mg, 60% hydrate, 4 mmol), and after stirring for 15 minutes at room temperature the temperature was again cooled to 0° C. Hexamethylphosphoric triamide (1.8 ml, 10 mmol) and then butyllithium (1.5 ml of a 2.5 M hexane solution, 3.8 mmol) were then added. After 20 minutes, methyl iodide (0.47 ml, 7.5 mmol) was added and stirring carried out for 1 hour. After returning to room temperature, the reaction was halted with dilute hydrochloric acid, after which the aqueous layer was extracted with dichloromethane, and then the organic layer dried with anhydrous sodium sulphate. The solution was concentrated, after which the residue obtained was subjected to separation and purification by column chromatography, and Compound 25 (625 mg, 74%) obtained as a pale yellow oily material.

Compound 25
High resolution mass spectrum
 Compositional formula C$_{13}$H$_{12}$O$_5$
 Calculated 248.0685
 Measured 248.0703
$^1$H-NMR (300 MHz, CD$_3$OD) δ=1.50 (d, J=7.14 Hz, 3H), 2.32 (d, J=0.82 Hz, 3H), 5.36 (q, J=7.14 Hz, 1H), 6.20 (q, J=0.82 Hz, 1H), 6.24–6.25 (m, 1H), 6.34–6.36 (m, 1H), 7.41–7.42 (m, 1H)
IR (KBr) cm$^{-1}$ 1729, 1644, 1615, 1557, 1458, 1236, 996
Mass (EI) 248 (M$^+$)s Example 26
Synthesis of Compound 26: 3-{2-(5-benzoylthiophene-2-yl)}acetyl-4-hydroxy-6-methyl-pyrone

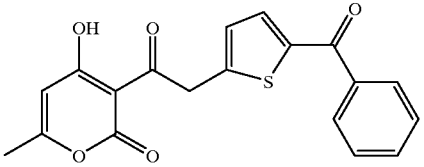

The reagent (TFOP) required for the acylation was prepared in the following manner in accordance with the literature. Sodium hydride (content 60%, 1.2 g) was washed with hexane and suspended in dioxane (25 ml). When 2-hydroxypyridine (2.8 g) was added at room temperature, heat was evolved and bubbling occurred. After the reaction had quietened down, stirring was carried out for 15 minutes at 40° C., the temperature then returned to room temperature and a THF (4 ml) solution of trifluoromethanesulphonyl chloride added dropwise. After stirring for 16 hours at room temperature, Celite filtration was carried out and the filtrate concentrated. When reduced pressure filtration (110–113° C./30 mmHg) was performed, 2-(trifluoromethylsulphonyloxy)pyridine (TFOP, 3.9 g, 58%) was obtained.

TFOP (750 mg, 3.0 mmol) was added to D62 (750 mg, 3.0 mmol) and benzoic acid (400 mg, 3.3 mmol), and trifluoroacetic acid (4 ml) added under a flow of argon. Then, heating and refluxing were performed for 2 days. Dichloromethane and dilute hydrochloric acid were added and extraction performed. The organic layer was dried with anhydrous sodium sulphate and concentrated, after which separation and purification were performed by column chromatography. When recrystallization was performed from ethanol, Compound 26 (560 mg, 53%) was obtained as violet crystals.

Compound 26
Melting point: 160–162° C. (dec)
Elemental analysis
    Compositional formula $C_{19}H_{14}O_5S$
    Calculated C, 64.40; H, 3.98
    Measured C, 63.91; H, 3.91
$^1$H-NMR (300 MHz, CDCl$_3$) δ=2.31 (d, J=0.82 Hz, 3H), 4.70 (d, J=0.70 Hz, 2H), 6.00 (q, J=0.82 Hz, 1H), 7.05 (td, J1=0.70 Hz, J2=3.83 Hz, 1H), 7.45–7.61 (m, 3H), 7.53 (d, J=3.83 Hz, 1H), 7.83–7.87 (m, 2H), 15.94 (br s, 1H)
IR (KBr) cm$^{-1}$ 1703, 1648, 1625, 1559, 1458, 1292, 996, 865, 707
Mass (EI) 354 (M$^+$)

Example 27
Synthesis of Compound 27: 3-{2-(5-acetylthiophene-2-yl)}acetyl-4-hydroxy-6-methyl-pyrone

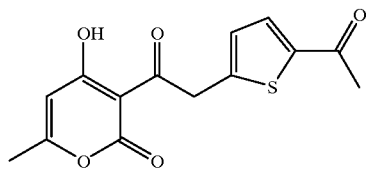

2-(Trifluoromethylsulphonyloxy)pyridine (TFOP, 750 mg, 3.0 mmol) was added to 3-(2-thiophene)acetyl-4-hydroxy-6-methyl-2-pyrone (750 mg, 3.0 mmol) and acetic acid (0.19 ml, 3.3 mmol), and then trifluoroacetic acid (4 ml) added under a flow or argon. Next, heating and refluxing were performed for 2 days. Dichloromethane and dilute hydrochloric acid were added and extraction performed. The organic layer was dried with anhydrous sodium sulphate and concentrated, after which separation and purification were performed by column chromatography, When recrystallization was performed from ethanol, Compound 27 (315 mg, %) was obtained as violet crystals.

Compound 27
Melting point: 146–149° C. (dec)
Elemental analysis
    Compositional formula $C_{14}H_{12}O_5S$
    Calculated C, 57.52; H, 4.14
    Measured C, 57.50; H 3.94
$^1$H-NMR (300 MHz, CDCl$_3$) δ=2.31 (d, J=0.82 Hz, 3H), 2.53 (s, 3H), 4.65 (d, J=0.70 Hz, 2H), 5.99 (q, J=0.82 Hz, 1H), 7.05 (td, J1=0.70 Hz, J2=3.83 Hz, 1H), 7.53 (d, J=3.83 Hz, 1H), 15.92 (br s, 1H)
IR (KBr) cm$^{-1}$ 1718, 1638, 1570, 1452, 1280, 997
Mass (EI) 292 (M$^+$)

Example 28
Synthesis of Compound 28: 3-{2-(3-methylthiophen-2yl)}acetyl-4-hydroxy-5-brom-6-methyl-pyrone

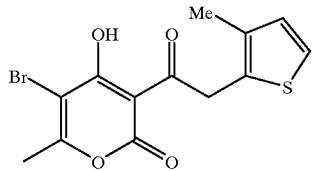

A chloroform (100 ml) solution of 4-hydroxy-6-methyl-3-propoxycarbonyl-2-pyrone (6.0 g, 28.3 mmol), synthesized from 4-hydroxy-6-methyl-2-pyrone and propyl chloroformate, was ice cooled, and a chloroform (100 ml) solution of bromine (4.0 ml, 78 mmol) and iodine (140 mg, 0.55 mmol) slowly added dropwise. After stirring for 7 days at 5° C., an aqueous sodium thiosulphate solution was added and separation performed. After drying and concentrating, crystallization was performed from ethanol and there was obtained the bromo-derivative, 5-bromo-4-hydroxy-6-methyl-3-propoxycarbonyl-2-pyrone (3.36 g, 41%), as white crystals.

Water (150 ml) and a few ml of methanol were added to this 5-bromo-4-hydroxy-6-methyl-3-propoxycarbonyl-2-pyrone (3.00 g, 10.3 mmol) and barium hydroxide hydrate (6.5 g, 20.6 mmol) and stirring carried out for 3 days at room temperature. After ice cooling, dilute hydrochloric acid was added dropwise, and dichloromethane separation and extraction performed. On drying and concentrating, the carboxylic acid formed by hydrolysis of the ester was obtained.

When this carboxylic acid was heated for 10 hours at 70° C. in ethanol, decarboxylation proceeded and 5-bromo-4-hydroxy-6-methyl-2-pyrone (740 mg, 35% yield for the two steps) was obtained as white crystals.

Chloroform (20 ml) was added to a mixture of the 5-bromo-4-hydroxy-6-methyl-2-pyrone (801 mg, 3.91 mmol), 3-methyl-2-thiopheneacetic acid (620 mg, 4.0 mmol) and dicyclohexylcarbodiimide (850 mg, 4.1 mmol). Then, 4-dimethylaminopyridine (70 mg, 0.57 mmol) was added and heating and refluxing carried out for 16 hours. On returning to room temperature, the dicyclohexylurea was filtered off and the reaction solution washed with dilute hydrochloric acid, after which the aqueous layer was extracted with dichloromethane. After drying with anhydrous sodium sulphate, the solvent was distilled off and separation and purification carried out by column chromatography. When recrystallization was carried out from ethanol, Compound 28 (390 mg, 29%) was obtained as white crystals.

Compound 28
Melting point: 122–123° C. (dec)
Elemental analysis

Compositional formula $C_{13}H_{11}BrO_4S$
Calculated C, 45.50; H, 3.23
Measured C, 45.51; H, 3.11
$^1$H-NMR (300 MHz, $CDCl_3$) δ=2.18 (s, 3H), 2.52 (s, 3H), 4.57 (s, 2H), 6.86 (d, J=5.0 Hz, 1H), 7.16 (d, J=5.0 Hz, 1H), 17.5 (s, 1H)
IR (KBr) $cm^{-1}$ 1729, 1614, 1542, 1457, 1188, 1024, 930
Mass (EI) 342 ($M^+$)

Example 29 synthesis of Compound 29: 3-(3-hexylthiophen-2yl)acetyl-4-hydroxy-6-methyl-pyrone and 3-(4-hexylthiophen-2-yl)acetyl-4-hydroxy-6-methylpyrone

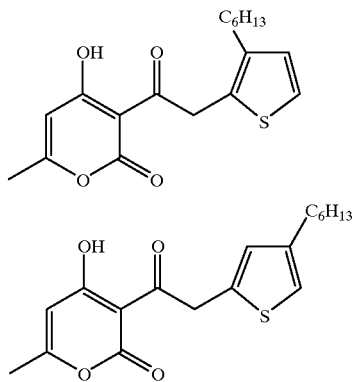

17.0 ml of phosphorus oxychloride was added dropwise to 14.0 ml of DMF and stirring carried out for 1 hour. 20.0 g (119 mmol) of 3-hexylthiophene was added dropwise to this and stirring carried out for 1 hour at 100° C. After cooling to room temperature, the reaction mixture was poured into ice-cooled aqueous sodium hydroxide solution, and extraction performed with dichloromethane. After drying and concentrating, purification was carried out by column chromatography, and 23.4 g (100%) of the 3- and 4-hexylthiophene-2-aldehydes obtained. The 3-hexyl: 4-hexyl ratio at this time was about 2:1.

The aldehyde mixture obtained was dissolved in 120 ml of THF, then 12.4 ml of methyl methylsulphinylmethyl sulphide and 9.5 ml of Triton B added, and refluxing carried out for 6 hours. After cooling to room temperature, concentration was performed. The residue was dissolved in dichloromethane and neutralized with dilute sulphuric acid. After drying and concentrating, 175 ml of 1 N HCl/ethanol was added to the residue and refluxing carried out for 6 hours. After cooling to room temperature and concentrating, the residue was purified by column chromatography and 27.9 g (91%) of the ethyl 3- and 4-hexylthiophene-2-acetates was obtained. 65 ml of 10% aqueous sodium hydroxide solution was added to the ester obtained and stirring carried out overnight at 80° C. After cooling to room temperature, the organic material was eliminated with ether, then the aqueous layer neutralized with concentrated hydrochloric acid and extraction performed with dichloromethane. Following drying and concentrating, 20.4 g (83%) of the 3- and 4-hexylthiophene-2-acetic acids was obtained.

The 20.4 g (90.5 mmol) of the 3- and 4-hexylthiophene-2-acetic acids, 11.4 g (90.4 mmol) of 4-hydroxy-6-methyl-2-pyrone and 20.5 g (99.3 mmol) of DCC were suspended in 200 ml of chloroform, and after stirring for 3 hours at room temperature, 1.1 g (9.01 mmol) of DMAP was added and stirring carried out overnight at 60° C. After cooling the reaction liquid to room temperature, the precipitated urea was filtered off, and the filtrate was extracted with aqueous sodium hydroxide solution. The aqueous layer was neutralized with concentrated hydrochloric acid and extracted with dichloromethane, after which drying and concentration were carried out. The residue was purified by column chromatography and 4.75 g (16%) of product obtained as an oily material. The 3- and 4-hexyl ratio at this time was about 5:2. The sodium salt was formed with an equivalent amount of sodium hydrogen carbonate.

Example 30

Growth promoting activity of IL-3 dependent myeloblastic cell line (1) Cells line and culture Murine IL-3 dependent myeloblastic cell line, FDC-P2 was used. The murine cell line was maintained in RPMI1640 medium supplemented with 10%(v/v) of FCS 0.05 mM of 2-mercaptoethanol and 10%(v/v) WEHI-3 conditioned medium as a source of IL-3.

(2) Compound dilution method

The compound was dissolved in DMSO to a 40 mM concentration, after which 10-fold dilution was performed with RPMI1640 medium to give a final concentration of 4 mM. Stepwise dilution was then carried out on a 96-well microplate.

(3) Addition of the IL-3

Murine IL-3 was diluted to 50 U/ml with RPMI1640 medium, and two-fold stepwise dilution carried out.

(4) Addition of cells

The cells (about $1\times10^7$ per ml) maintained in (1) were centrifuged at 1000 rpm for 5 minutes at 4° C., after which the supernatant was eliminated, and re-suspendedin 10 ml of RPMI1640. This procedure was repeated three times to remove the IL-3 contained in the medium. Subsequently, using ahemocytometer, the cell concentration was measured and a cell suspension of concentration $2\times10^5$ cells/ml produced. 50 ml of this was seeded in each well and culturing carried out for 20 hours at 37° C.

(5) Measurement of the cell growth by the MTT method

This was carried out based on the MTT measurement method of Mosmann et al. 10 ml quantities of the MTT of concentration 5 mg/ml were added to each well of the plate on which cellshad been incubatedfor 20 hours in (4), and further culturing carried out for 4 hours. Subsequently, 100 ml of 10% (SDS)/0.01 N-HCl solution was added per well and the MTT formazan was dissolved by warming at 37° C. overnight. Absorbance(620 nm) of each well was mesured in an Immunoreader.

(6) Calculation of the measured absorbance and the conversion of units

A regression line was drawn based on the absorbance of an IL-3 50 U/ml control for each plate, and then the number of units calculated based on the absorbance for each series based on the ED 50 value thereof. A control plate of DMSO alone was set, and the percentage increase calculated with reference thereto.

The results are shown in Table 1.

TABLE 1

| Compound | Concentration (µM) | Percentage Growth |
|---|---|---|
| 1 | 500 | 119 |
| 2 | 250 | 140 |
| 3 | 125 | 134 |
| 4 | 250 | 181 |

Example 31
Haemopoietic activity in ordinary mice

Using Compound 4 as the test drug, this was administered intravenously for a four days to C57BL/6 mice (6 weeks old, male) (n=6) at a dose of 10 mg/kg, and 7 days outset of injection the number of blood cells in the peripheral blood was measured.

FIG. 1 shows the percentage increase in terms of a control group (taken as 100%). From the results, it is clear that the test drug significantly increased the number of red blood cells, demonstrating the value of the compounds described in this patent as haemopoietic agents.

Industrial Utilization Potential

The cyclic ketones of the present invention bring about a significant increase in red blood cells and other cells, and they are effective as outstanding haemopoietic agents in medicine, in particular for the prevention or treatment of cytopaenia brought about by cancer chemotherapy, radiotherapy, bone marrow transplantation or drug therapy, or by immunological abnormality or anaemia.

What is claimed is:

1. A cyclic ketone compound represented by formula (I):

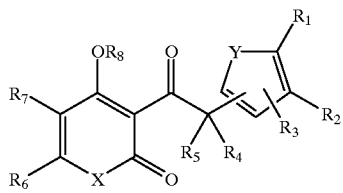

where $R^1$, $R_2$ and $R_3$ are independently a hydrogen atom, fluorine atom, chlorine atom, bromine atom, $C_1$ to $C_{10}$ alkyl group, $C_1$ to $C_{10}$ alkenyl group, $C_1$ to $C_{10}$ alkynyl group, $C_6$ to $C_{12}$ aryl group, $C_6$ to $C_{12}$ arylalkyl group, $C_6$ to $C_{12}$ alkylaryl group, $C_6$ to $C_{12}$ arylalkenyl group, or —$(CH_2)_pZ$ (where p represents an integer in the range 0 to 3, and Z represents a cyano group, carboxyl group, methylthio group, phenylthio group, trifluoromethyl group or methylthiomethyl group, with the proviso that $R_1$, $R_2$ and $R_3$ are not all substituents selected from the hydrogen atom, fluorine atom, chlorine atom and bromine atom, $R_4$ and $R_5$ respectively independently represent a hydrogen atom, fluorine atom, chlorine atom, bromine atom, $C_1$ to $C_6$ alkyl group, hydroxy group, $C_1$ to $C_6$ alkoxy group, carboxy group or $C_2$ to $C_{10}$ alkoxycarbonyl group, $R_6$ represents a hydrogen atom, fluorine atom, chlorine atom, bromine atom, $C_1$ to $C_{10}$ alkyl group, $C_6$ to $C_{12}$ aryl group, $C_6$ to $C_{12}$ arylalkyl group, $C_6$ to $C_{12}$ alkylaryl group, $C_6$ to $C_{12}$ arylalkenyl group, or —$(CH_2)_qG$ (where q represents an integer in the range 1 to 3, and G represents a hydroxyl group or $C_2$ to $C_{10}$ alkoxycarbonyl group), $R_7$ represents a hydrogen atom, fluorine atom, chlorine atom, bromine atom, $C_1$ to $C_{10}$ alkyl group, $C_6$ to $C_{12}$ aryl group, carboxy group or $C_2$ to $C_{10}$ alkoxycarbonyl group, $R_8$ represents a hydrogen atom or $C_1$ to $C_{10}$ alkyl group, X is O or S, and Y is O or S, or pharmacologically acceptable salts thereof.

2. The cyclic ketone compound or pharmacologically acceptable salt thereof according to claim 1, where $R_1$ to $R_5$ are independently a hydrogen atom, fluorine atom, chlorine atom, bromine atom, $C_1$ to $C_{10}$ alkyl group, or substituted or unsubstituted phenyl group, and $R_6$ and $R_7$ are independently a hydrogen atom, fluorine atom, chlorine atom, bromine atom, $C_1$ to $C_{10}$ alkyl group, or substituted or unsubstituted phenyl group.

3. The cyclic ketone compound of pharmacologically acceptable salt thereof according to claim 1, where $R_6$ represents a hydrogen atom, fluorine atom, chlorine atom, bromine atom, $C_1$ to $C_{10}$ alkyl group, $C_6$ to $C_{12}$ aryl group, $C_6$ to $C_{12}$ arylalkyl group, $C_6$ to $C_{12}$ alkylaryl group, $C_6$ to $C_{12}$ arylalkenyl group, or —$(CH_2)_qG$ (where q represents an integer in the range 1 to 3, and G represents a hydroxyl group or $C_2$ to $C_{10}$ alkoxycarbonyl group), and $R_7$ represents a hydrogen atom, fluorine atom, chlorine atom, bromine atom, $C_1$ to $C_{10}$ alkyl group, $C_6$ to $C_{12}$ aryl group, carboxy group or $C_2$ to $C_{10}$ alkoxycarbonyl group.

4. The cyclic ketone compound or pharmacologically acceptable salt thereof according to claim 1, where $R_1$ to $R_3$ are independently a hydrogen atom, fluorine atom, chlorine atom, bromine atom, $C_1$ to $C_{10}$ alkyl group, or substituted or unsubstituted phenyl group, $R_4$ is a hydrogen atom, $R_5$ is a hydrogen atom, $R_6$ is a hydrogen atom, $C_1$ to $C_{10}$ alkyl group, or substituted or unsubstituted phenyl group, $R_7$ is a hydrogen atom, fluorine atom, chlorine atom, bromine atom, $C_1$ to $C_{10}$ alkyl group, or substituted or unsubstituted phenyl group, or and $R_8$ is a hydrogen atom.

5. A pharmaceutical composition comprising the cyclic ketone compound of claim 1 or pharmacologically acceptable salt thereof together with a pharmaceutically acceptable carrier or diluent.

6. A method for the treating or preventing cytopaenia comprising administering to a subject in need of same an effective amount of the compound of claim 1 or pharmacologically acceptable salt thereof.

7. A method for increasing blood cells comprising administering to a subject in need of same an effective amount of a cyclic ketone compound of claim 1 or pharmacologically acceptable salt thereof.

8. A process for preparing a cyclic ketone compound according to claim 1 comprising condensing a ketone represented by formula (II) and a carboxylic acid or carboxylic acid derivative represented by formula (III)

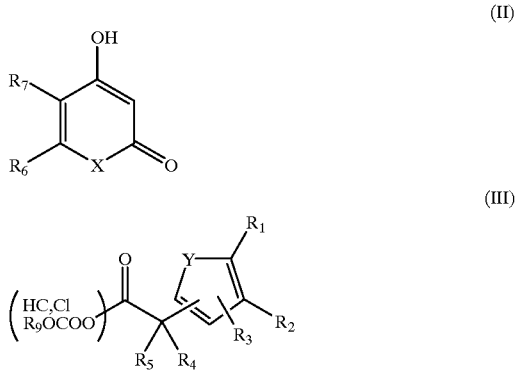

where $R_1$, $R_2$ and $R_3$ are independently a hydrogen atom, fluorine atom, chlorine atom, bromine atom, $C_1$ to $C_{10}$ alkyl group, $C_1$ to $C_{10}$ alkenyl group, $C_1$ to $C_{10}$ alkynyl group, $C_6$ to $C_{12}$ aryl group, $C_6$ to $C_{12}$ arylalkyl group, $C_6$ to $C_{12}$ alkylaryl group, $C_6$ to $C_{12}$ arylalkenyl group, —$(CH_2)_pZ$ (where p represents an integer in the range 0 to 3, and Z represents a cyano group, carboxyl group, methylthio group, phenylthio group, trifluoromethyl group or methylthiomethyl group with the proviso that $R_1$, $R_2$ and $R_3$ are all not substituents selected from hydrogen atom, fluorine atom, chlorine atom and bromine atom, $R_4$ and $R_5$ respectively independently represent a hydrogen atom, fluorine atom, chlorine atom, bromine atom, $C_1$ to $C_6$ alkyl group, hydroxyl group, $C_1$ to $C_6$ alkoxy group, carboxy group or $C_2$ to $C_{10}$ alkoxycarbonyl group, $R_6$ represents a hydrogen atom, fluorine atom, chlorine atom, bromine atom, $C_1$ to $C_{10}$ alkyl group, $C_6$ to $C_{12}$ aryl group, $C_6$ to $C_{12}$ arylalkyl group, $C_6$ to $C_{12}$ alkylaryl group, $C_6$ to $C_{12}$ arylalkenyl group, —$(CH_2)_qG$ (where q represents an integer in the range 1 to 3, and G represents a hydroxyl group or $C_2$ to $C_{10}$ alkoxycarbonyl group), $R_7$ represents a hydrogen atom, fluorine atom, chlorine atom, bromine atom, $C_1$ to $C_{10}$ alkyl group, $C_6$ to $C_{12}$ aryl group, carboxy group or $C_2$ to $C_{10}$ alkoxycarbonyl group, $R_8$ represents a hydrogen atom or a $C_1$ to $C_{10}$ alkyl group, X represents O or S, Y represents O or S, and $R_9$ is a $C_1$ to $C_{10}$ alkyl group or a phenyl group.

9. The process of claim 8, where $R_6$ represents a hydrogen atom, fluorine atom, chlorine atom, bromine atom, $C_1$ to $C_{10}$ alkyl group, $C_6$ to $C_{12}$ aryl group, $C_6$ to $C_{12}$ arylalkyl group, $C_6$ to $C_{12}$ alkylaryl group, $C_6$ to $C_{12}$ arylalkenyl group, or —$(CH_2)_qG$ (where q represents an integer in the range 1 to 3, and G represents a hydroxyl group or $C_2$ to $C_{10}$ alkoxycarbonyl group), and $R_7$ represents a hydrogen atom, fluorine atom, chlorine atom, bromine atom, $C_1$ to $C_{10}$ alkyl group, $C_6$ to $C_{12}$ aryl group, carboxy group or $C_2$ to $C_{10}$ alkoxycarbonyl group.

* * * * *